US010751582B2

United States Patent
Dolezel et al.

(10) Patent No.: US 10,751,582 B2
(45) Date of Patent: Aug. 25, 2020

(54) SPORTING APPARATUS WITH MONITORING DEVICE

(71) Applicant: Dunlop Sports Co., Ltd., Kobe-shi, Hyogo (JP)

(72) Inventors: Keith Dolezel, West Covina, CA (US); Scott Carlyle, Costa Mesa, CA (US); Michael J. Kline, Corona Del Mar, CA (US)

(73) Assignee: DUNLOP SPORTS CO. LTD, Hyogo (JP)

( * ) Notice: Subject to any disclaimer, the term of this patent is extended or adjusted under 35 U.S.C. 154(b) by 87 days.

(21) Appl. No.: 15/671,571

(22) Filed: Aug. 8, 2017

(65) Prior Publication Data

US 2018/0021636 A1    Jan. 25, 2018

Related U.S. Application Data

(62) Division of application No. 14/564,933, filed on Dec. 9, 2014, now Pat. No. 9,731,172.

(51) Int. Cl.
*A63B 60/46* (2015.01)
*A63B 69/00* (2006.01)
(Continued)

(52) U.S. Cl.
CPC ............ *A63B 53/04* (2013.01); *A63B 53/047* (2013.01); *A63B 60/02* (2015.10); *A63B 60/46* (2015.10); *A63B 60/50* (2015.10); *A63B 69/3632* (2013.01); *G06F 19/3481* (2013.01); *G06K 9/00342* (2013.01); *G06Q 10/0639* (2013.01); *G09B 19/0038* (2013.01); *H04M 1/7253* (2013.01); *A63B 60/54* (2015.10); *A63B 69/0015* (2013.01); *A63B 69/0017* (2013.01); *A63B 69/0024* (2013.01); *A63B 69/38* (2013.01); *A63B 71/0622* (2013.01);
(Continued)

(58) Field of Classification Search
CPC ..... A63B 69/3632; A63B 60/46; A63B 53/04; A63F 13/211; G06K 9/00342
See application file for complete search history.

(56) References Cited

U.S. PATENT DOCUMENTS 6,441,745 B1    8/2002   Gates
8,109,816 B1 *  2/2012   Grober ............... A63B 69/3632
                                                463/3
(Continued)

FOREIGN PATENT DOCUMENTS

EP           2701814 A1    3/2014

*Primary Examiner* — David L Lewis
*Assistant Examiner* — Robert E Mosser
(74) *Attorney, Agent, or Firm* — BakerHostetler

(57) ABSTRACT

A sporting apparatus includes a monitoring device. The monitoring device may add no weight to the sporting apparatus relative to a comparable sporting apparatus without the monitoring device. The monitoring device may have a center of gravity substantially aligning with the center of gravity of the sporting apparatus, resulting in a sporting apparatus with a monitor having substantially the same center of gravity as a comparable sporting apparatus without a monitor. The sporting apparatus monitor may be configured to trim unreliable post impact swing data and replace it with extrapolated pre-impact swing data and/or more reliable post impact swing data.

20 Claims, 14 Drawing Sheets

(51) Int. Cl.
*A63B 71/06* (2006.01)
*A63B 53/04* (2015.01)
*G06F 19/00* (2018.01)
*G06Q 10/06* (2012.01)
*G06K 9/00* (2006.01)
*G09B 19/00* (2006.01)
*H04M 1/725* (2006.01)
*A63B 69/36* (2006.01)
*A63B 60/02* (2015.01)
*A63B 60/50* (2015.01)
*A63B 69/38* (2006.01)
*A63B 71/14* (2006.01)
*A63B 60/54* (2015.01)

(52) U.S. Cl.
CPC ..... *A63B 71/146* (2013.01); *A63B 2053/0433* (2013.01); *A63B 2053/0491* (2013.01); *A63B 2069/0008* (2013.01); *A63B 2220/20* (2013.01); *A63B 2220/44* (2013.01); *A63B 2220/801* (2013.01); *A63B 2225/50* (2013.01)

(56) References Cited

U.S. PATENT DOCUMENTS

| | | | |
|---|---|---|---|
| 8,172,692 | B2 | 5/2012 | Price et al. |
| 8,172,694 | B2 | 5/2012 | Golden et al. |
| 8,591,352 | B2 | 11/2013 | Hirano |
| 8,668,595 | B2 | 3/2014 | Boyd et al. |
| 8,696,482 | B1 | 4/2014 | Pedenko et al. |
| 2006/0084516 | A1* | 4/2006 | Eyestone ............ A63B 69/3632 473/219 |
| 2010/0093463 | A1 | 4/2010 | Davenport et al. |
| 2010/0331102 | A1 | 12/2010 | Golden et al. |
| 2011/0224012 | A1* | 9/2011 | Hashimoto ........ A63B 69/3632 473/223 |
| 2013/0102419 | A1 | 4/2013 | Jeffery et al. |
| 2013/0267338 | A1 | 10/2013 | Boyd et al. |
| 2014/0200094 | A1* | 7/2014 | Parke ...................... A63F 13/00 473/223 |

* cited by examiner

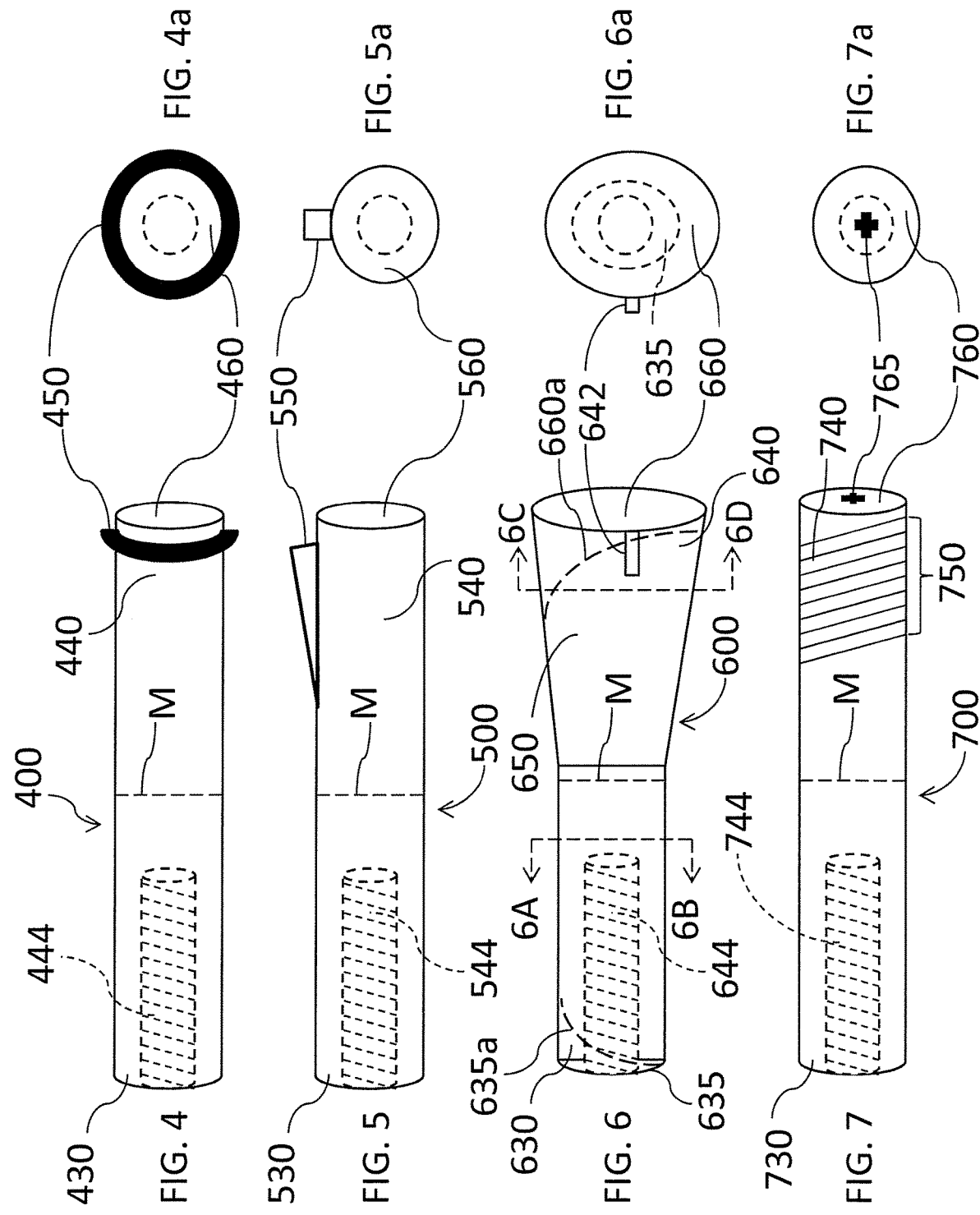

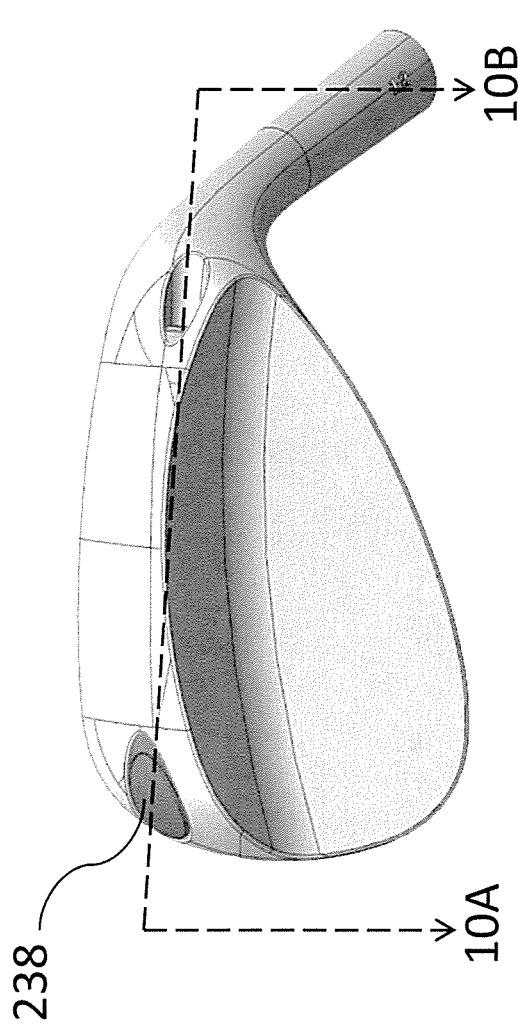
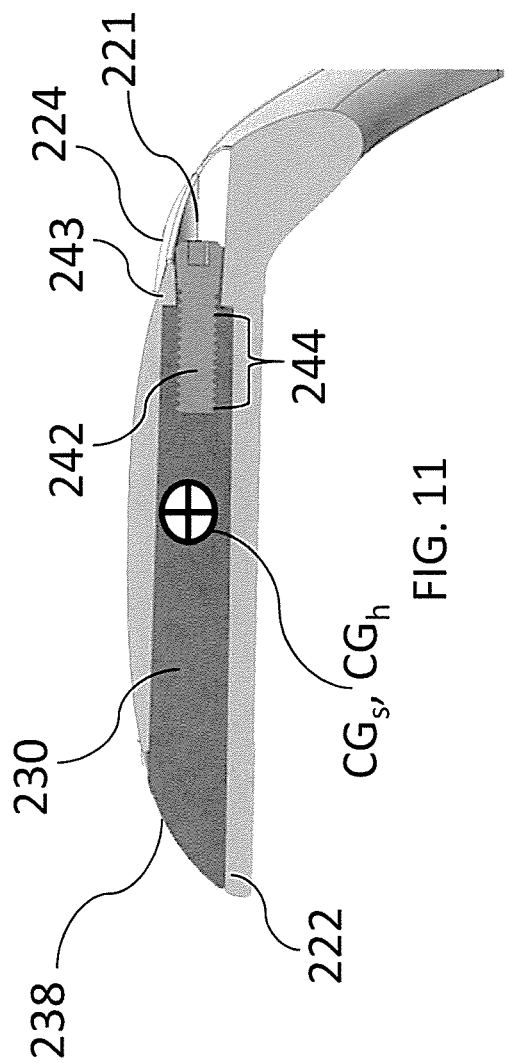
FIG. 10
FIG. 11

SPORTING APPARATUS WITH MONITORING DEVICE

CROSS REFERENCE TO RELATED APPLICATIONS

This application is a divisional of, and claims priority to, U.S. patent application Ser. No. 14/564,933, filed Dec. 9, 2014, entitled "Sporting Apparatus With Monitoring Device," the entire contents of which are hereby incorporated herein by reference.

BACKGROUND

Golfers and other sports enthusiasts are constantly looking for ways to improve their game. Golfers in particular are relying more heavily on technological innovations to enhance whatever natural abilities they have. Such innovations take the form of improved golf equipment such as golf clubs, golf shoes, golf gloves, golf balls, and even golf attire.

Golfers and golf club equipment manufacturers have been increasingly relying upon sensors and monitors to evaluate a golfer's swing. Sensors and monitors may track conditions, such as club head speed, attack angle, launch angle, golf ball spin rate and spin direction, and so on. And sellers of golf club equipment, including outlets that specialize in golf club fitting, increasingly rely on such sensors and monitors to assist a prospective purchaser in selecting golf clubs that best match their particular golf swing characteristics.

One such sensor that is commercially available is the SB2 sensor available from Swingbyte, LLC (previously Swingbyte, Inc.) of Chicago, Ill. Such sensors, as described in U.S. Pat. No. 8,696,482, incorporated in its entirety by reference herein, are typically removeably attached to the shaft of a golf club, for example with a clamping mechanism, or fixed to the shaft, for example, with an adhesive. Such sensors, also termed "three-dimensional golf swing analyzers," work as an Inertial Measurement Unit (IMU), and typically include, for example, a three-axis accelerometer capable of producing and transmitting linear acceleration data, a three-axis gyroscope capable of producing and transmitting angular velocity data, a first microprocessor that receives data from the accelerometer and the gyroscope and processes the data, a first computer memory wherein the microprocessor stores the processed data, and a radio transmitter for transmitting the processed data from the first computer memory. MEMS (microelectromechanical systems) technology may be used for the accelerometer and the gyroscope. The sensor is typically powered by a battery or other suitable power source. A housing is used to hold the microprocessor, accelerometer, gyroscope computer memory, radio transmitter, and battery.

Such devices capture and analyze golf swing (or other sporting apparatus motion) data by attaching a sensor to a golf club either below the grip or on the cap, or by integrating the sensor into the shaft. After hitting a shot or swinging the golf club (or other sporting apparatus) players and instructors can view an interactive, three-dimensional animation of the swing, along with key metrics, such as club head speed, path, plane, and various angles at impact. It is generally preferred to affix such sensors at a position remote from the golf club head, due to the head's tendency to vibrate violently at the point of impact, potentially disrupting the sensor's attempts to measure the swing characteristics. Such sensors use a transmitter to send processed linear and angular movement data that defines a sporting apparatus swing, i.e., a golf club swing, to a receiver on a mobile device, such as a smart phone, tablet computer, or laptop computer. A computer application running on the mobile device receives the processed data, processes the data further and displays a graphical representation of the entire swing with comprehensive statistics for every point of the swing. The processed data is stored and later used along with theoretical data to coach a golfer or other sporting apparatus user on his or her swing.

But attaching such sensors, whether to the shaft of a golf club or otherwise, can alter the golfer's normal swing and feel due to the weight of the sensor, which may be 10-50 grams and more commonly around 30 grams. For a 300 gram driver, for example, a 30 gram sensor thus represents a 10% deviation from the club's playing weight. Such added weight may be particularly noticeable to better players, and in particular tour professionals. Moreover, attaching such sensors to the shaft may not be the ideal location for at least three reasons: first, the sensor may be visible/distracting to the player when positioned on the shaft, second, the sensor may be positioned at inconsistent positions along the shaft from club to club or player to player, and third, positioning on the shaft may not be the most beneficial position from which to monitor the user's swing pattern.

Specific to this third point, attaching a sensor to the golf club shaft, for example near the grip, may not precisely monitor the path of the golf club, because during the swing, the shaft flexes, and at impact, the golf club head slows slightly, while the math governing the swing visualization assumes the shaft is substantially rigid and not flexing, so no accelerations to directions other than where the hands seem to be guiding a completely rigid shaft are accounted for. The projected swing path thus follows where the hands would project a rigid cylinder during a swing.

U.S. Patent Application Publication No. US 2013/0267338 A1, incorporated in its entirety by reference herein, discloses a monitoring device including a sensor and transmitter, which may be attached to a golf club head and may be configured to transmit data related to the characteristics of a golf swing to a remote computer.

A problem, however, with mounting sensors in the golf club head is that off center hits (heel or toe, high face/low face), tend to cause the head to wobble back and forth, from the point of impact through a portion of the follow through, for example about half way through the follow through (when the club passes waist height). The accelerometer/gyroscopes/IMUs pick up such club head wobble, and depending on the math driving the algorithm, these forces/accelerations in unusual directions (depending on where the sensor is located) may adversely affect the projected swing path visualization. Moreover, there will be more twisting forces at takeaway (as the shaft torques and hands are rotated). There will be potentially unreliable data at the top of the swing from transition from backswing to downswing (where the shaft flexes quite a bit). With this flex, the orientation of the head to the original (static) might be off 5-10 degrees and twisted 2-5 degrees. At impact, again, the flex and wobble may tend to cause some accelerations. Back and forth oscillation and also at impact, the shaft usually flexes so that the head is flung in front of the static shaft plane and oriented inside the plane (closer to the feet) as the dynamic movement causes the center of gravity of the head to align with the center of gravity of the club.

SUMMARY

The following presents a general summary of aspects of the disclosure in order to provide a basic understanding thereof. This summary is not an extensive overview of the disclosure. It is not intended to identify key or critical elements of the disclosure or to delineate the scope of the disclosure. The following summary merely presents some concepts of the disclosure in a general form as a prelude to the more detailed description provided below. The present disclosure describes a golf club head comprising a monitoring device configured, when placed within the golf club head, to add substantially no mass relative to a comparable golf club head without the monitoring device, the monitoring device configured to transmit data responsive to a pre-impact swing path of the golf club head, to disregard or trim data responsive to a post-impact swing path, and to determine a hypothetical post-impact swing path based at least in part on at least a portion of the pre-impact swing path.

In another aspect, the golf club head may further comprise a sole portion and a face portion, the sole portion comprising a hollow sized and shaped to compliment the monitoring device when the monitoring device is placed within the hollow, the hollow having a volume corresponding to a mass of displaced material from the golf club head, the mass of displaced material substantially equaling the mass of the monitoring device as installed in the golf club head.

In another aspect, the monitoring device may be further configured to determine the hypothetical post-impact swing path based at least in part on at least a portion of the pre-impact swing path and at least in part on a portion of the post-impact swing path.

In still another aspect of the disclosure, the hypothetical post-impact swing path may comprise a path from a point of impact of the golf club head with a golf ball until a point substantially corresponding to a post-impact position at which post-impact golf club head vibrations have substantially ceased.

Yet another aspect of the disclosure may provide a system comprising a remote device and a sporting apparatus comprising a first monitoring device and a second monitoring device, the first monitoring device and second monitoring device being spaced apart relative to a longitudinal axis of the sporting apparatus and secured to the sporting apparatus, the first monitoring device and second monitoring device each comprising a monitoring device configured to transmit data corresponding to a swing of the sporting apparatus to the remote device, the system configured to:
 a. determine which of the first monitoring device and the second monitoring device is, during a first portion of the swing of the sporting apparatus, transmitting data most reflective of the first portion of swing of the sporting apparatus,
 b. capture the data most reflective of the first portion of the swing of the sporting apparatus,
 c. determine which of the first monitoring device and the second monitoring device is, during a second portion of the swing of the sporting apparatus, transmitting data most reflective of the second portion of the swing of the sporting apparatus,
 d. capture the data most reflective of the second portion of the swing of the sporting apparatus, and
 e. accumulate the data most reflective of the first portion of the swing of the sporting apparatus with the data most reflective of a second portion of the swing of the sporting apparatus.

BRIEF DESCRIPTION OF THE DRAWINGS

The present disclosure is illustrated by way of example and not limited in the accompanying figures, in which like reference numerals indicate similar elements throughout, and in which:

FIG. 4 is a schematic illustration of an exemplary monitoring device of the present disclosure.

FIG. 4a is an exemplary securing structure for a monitoring device.

FIG. 5 is another schematic illustration of an exemplary monitoring device of the present disclosure.

FIG. 5a is an exemplary securing structure for a monitoring device.

FIG. 6 is another schematic illustration of an exemplary monitoring device of the present disclosure.

FIG. 6a an exemplary securing structure for a monitoring device.

FIG. 7 is another schematic illustration of an exemplary monitoring device of the present disclosure.

FIG. 7a is an exemplary securing structure for a monitoring device.

FIG. 10 is a perspective view of a sporting apparatus of the present disclosure with a monitoring device of the present disclosure installed therein.

FIG. 11 is a cross-sectional view along line 10A-10B of the sporting apparatus of FIG. 10.

DETAILED DESCRIPTION

As used herein, the term "sporting apparatus" means an object intended to be used in a game or sport by swinging at, capturing, hitting, throwing, or otherwise impacting another object (sports object) such as a ball, puck, etc. including in both the actual and virtual realms. A sporting apparatus includes, but is not limited to baseball bats, cricket bats, golf clubs, hockey sticks, tennis rackets, squash rackets, racquetball rackets, badminton rackets, or lacrosse sticks, and further includes devices such as video game controllers intended to mimic such sporting apparatus. A "sporting apparatus" may impact or be associated with an impact with device such as a sporting object, and thus may also, for example, include a shoe configured to kick a soccer ball or football, or apparel, such as a golf glove, body suit, or helmet, that a user might wear when causing an impact. A sporting apparatus may have an impact area, which is an area of the sporting apparatus that normally impacts another sporting apparatus or sports object when participating in a sport. For example, an impact area may include some or all of a golf club head (i.e., golf club head 1510) for golf, bat barrel for baseball, or the like. A non-impact area may be an area of the sporting apparatus that is not normally impacted by another sporting apparatus, such as a golf club shaft (i.e., shaft 1520), racket handle, bat handle, or the like. While the disclosure refers, for convenience, primarily to golf clubs, golf club heads, and golf-related equipment, it should be understood that this is for brevity only, and that the teachings and disclosures herein are intended to apply to any sporting apparatus and not merely golf clubs.

Figure 1:
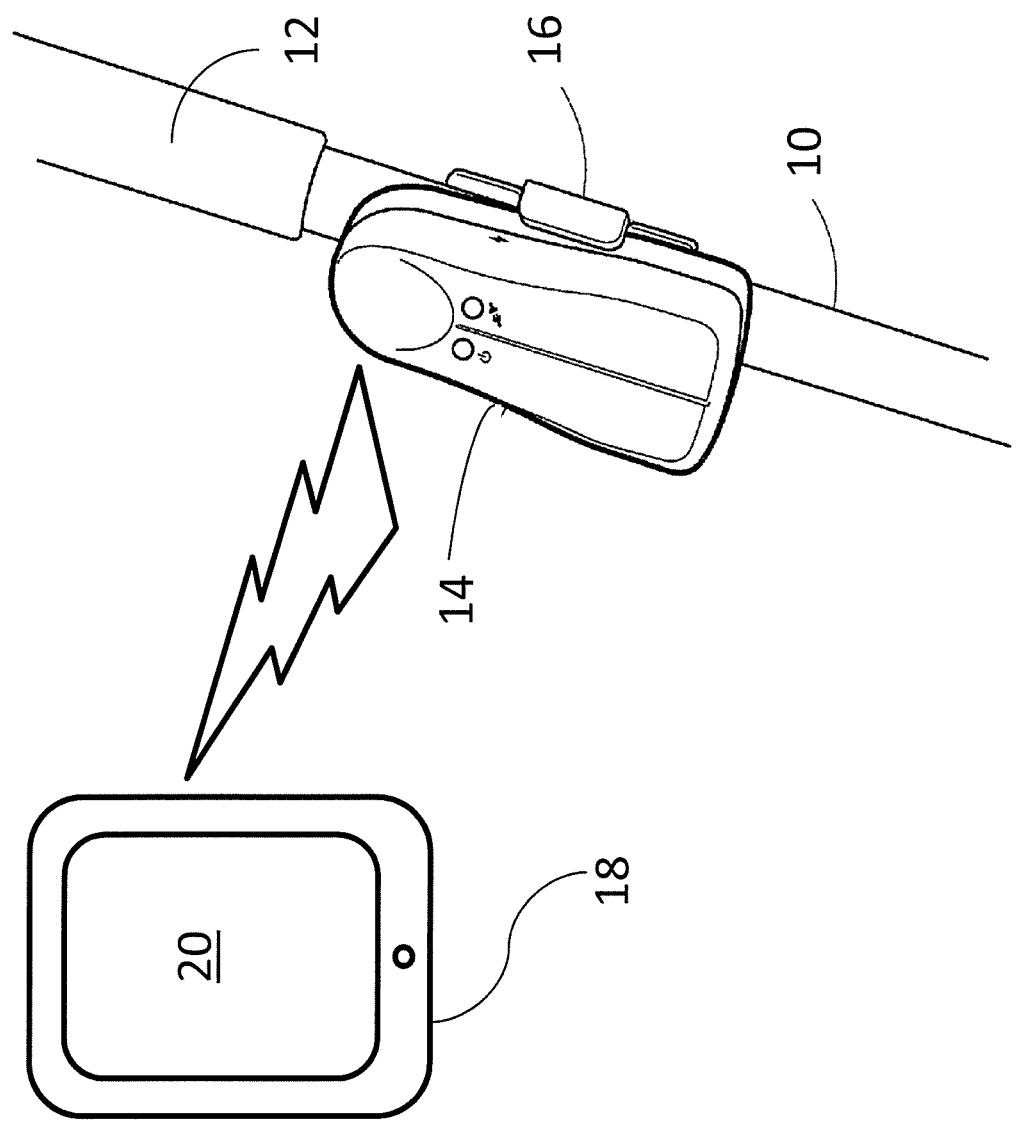
FIG. 1 is an illustration of a monitoring device of the prior art attached to a sporting apparatus, such as a golf club shaft.

Referring to FIG. 1, there is illustrated a sporting apparatus comprising a golf club shaft, generally 10, of the prior art, having a golf club head (not shown) affixed to a golf club shaft 10 and including a golf club grip 12. Also illustrated in FIG. 1 is a monitoring device 14, such as the Swingbyte SB2 sensor previously described, attached to the golf club shaft 10 as is known, for example, with a clamp or strap 16. Such monitoring devices 14 may be configured to transmit information, data, graphics, etc. to a remote device 18, such as a computer, laptop, tablet, smart phone, etc., where it may be accessed, displayed, or monitored on a display 20.

Figure 2:
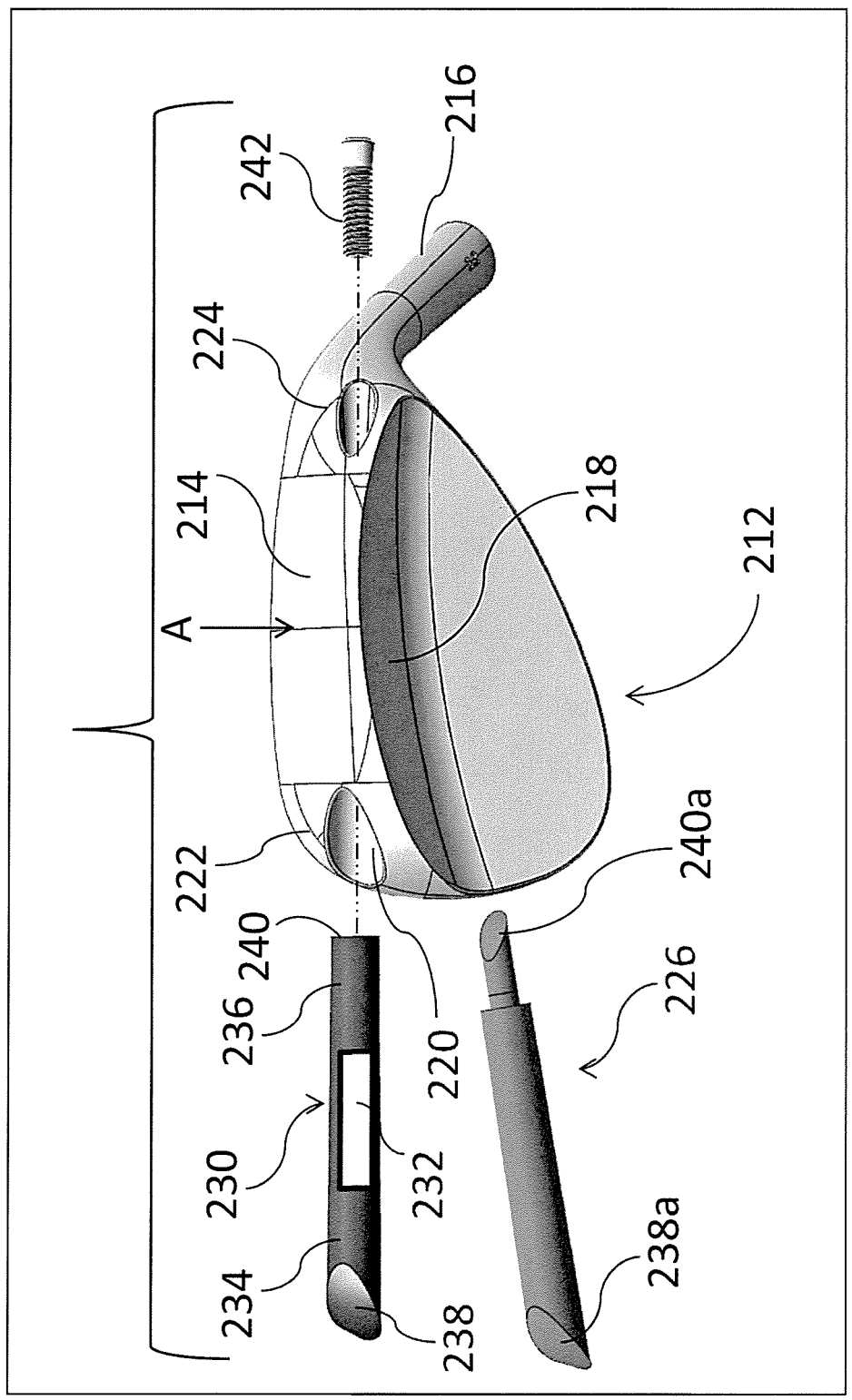
FIG. 2 is an exploded view of a portion of a sporting apparatus of the present disclosure, such as a golf club head with a monitoring device configured to be placed therein.

Referring now to FIG. 2, there is illustrated an aspect of the disclosure comprising a golf club head, generally 212. In this example, the golf club head 212 may comprise an iron type golf club head, for example, a wedge, having a sole 214, a hosel 216, a back or "muscle" portion 218, and a face (not shown). As illustrated, the golf club head 212 may comprise a hollow portion 220. The hollow portion 220 may be forged as part of the golf club head, cast in, drilled out, milled in, or otherwise formed in the golf club head 212. In this example, the hollow portion 220 may be formed in the region of the golf club head proximate to or comprising the sole 214. The hollow portion 220 may pass from a toe region 222 through the sole to a heel region 224 as illustrated, or may "dead end" within the golf club head 212, for example, and may thus comprise only one entry point. While the hollow portion 220 is illustrated in FIG. 2 as "tunneling" into the sole 214, it will be appreciated that the hollow portion 220 may comprise an open channel, indentation, groove, or other type of recess of sufficient size and shape to receive all or a substantial portion of a monitoring device therein. Although the golf club head 212 of FIG. 2 is illustrated as an iron-type golf club head, the present disclosure is intended to cover any type of golf club or head therefore, including drivers, fairway woods, hybrids, irons, and putters.

The hollow portion 220 may result in an undesirable loss of weight of the golf club head 212 relative to the golf club grip 12 of FIG. 1. This loss of weight or mass is illustrated schematically by a hypothetical plug of material, generally 226, of FIG. 2, having a displaced mass of $M_1$. The hypothetical plug of material 226 may have a volume substantially equal to the volume of the hollow portion 220, assuming the hollow portion 220 has contoured ends complimenting the toe region 222 and heel region 224. Of course, different configurations for the hypothetical plug of material 226 are possible, depending on the size, shape, location, etc., of the hollow portion 220. As will be subsequently described, an aspect of the present disclosure may compensate for this displaced mass $M_1$ with an appropriately weighted and/or configured monitoring device, and thereby minimize or even eliminate any perceptible difference in swing weight and swing feel between a golf club without a monitoring device and a golf club with a monitoring device.

Figure 3:
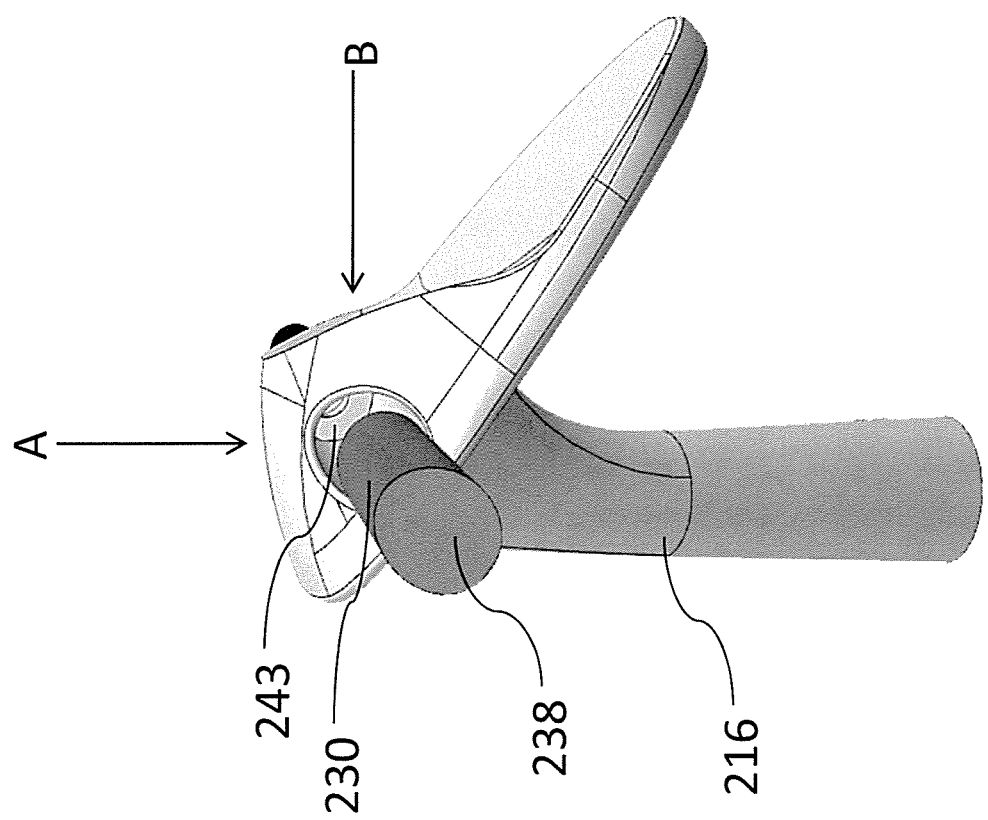
FIG. 3 is a left side view of the golf club head and monitoring device of FIG. 2.

As further illustrated in FIGS. 2 and 3, a monitoring device, generally 230, may be configured to be installed in the hollow portion 220. As illustrated in FIG. 11, the hollow portion 220 may run from the toe region 222 to the heel region 224 to create a passageway through the golf club head 212 with two open ends. In this aspect, as best seen in FIG. 11, one end of the hollow portion 220 passageway, for example, that portion exiting the heel region 224, may comprise an access 221 configured to receive a threaded bolt or screw 242. In this aspect, the threaded bolt or screw 242 may be threadably received by a female threaded region 244 in either the end 238 or the end 240 of the monitoring device 230. Although a threaded bolt or screw 242 is illustrated and described for the sake of convenience, it will be understood that any suitable securing structure may be employed to secure the monitoring device 230 within the golf club head 212, including by way of example but not limitation, pins, rivets, detents, press fit structures, clamps, and the like.

Alternatively, the hollow portion 220 may be formed in the golf club head 212 with just one open end terminating in a "dead end" within the golf club head 212. In this aspect, the monitoring device 230 may be configured with an external thread configured to be threadably received in a female threaded region in the wall of the hollow portion 220 (not shown). As yet another alternative, the monitoring device may be configured to receive one or more pins, threaded bolts, or screws through the golf club head in a direction generally perpendicular to the hollow portion 220, i.e., as illustrated by arrows "A" and "B" (FIG. 3) for retaining the monitoring device 230 in the golf club head.

In a preferred aspect, the monitoring device 230 may comprise a size and shape substantially corresponding to the hollow portion 220 and/or to the hypothetical plug of material 226 represented by the hollow portion 220. In a highly preferred aspect, the monitoring device 230 may be configured to have a mass $M_2$ substantially equal to the mass $M_1$ of the hypothetical plug of material 226. This mass $M_2$ may be achieved, for example, by employing a monitoring device 230 comprising a sensor component 232, which may comprise, for example, an accelerometer, transmitter, battery, etc. The monitoring device 230 and/or sensor component 232, however, may be smaller than the hollow portion 220 and/or may comprise less mass than $M_1$. It may therefore be advantageous to include as part of the monitoring device 230 one or more "fill" and/or "weighting" elements, such as a weighted portion 234 and/or a filler portion 236. The weighted portion 234 may comprise a relatively high mass material, such as metal, i.e., tungsten, copper, lead, etc., while the filler portion, if used, may comprise a relatively light weight material, i.e., a light weight polymer. Some portion or the entire monitoring device 230 may be housed in a protective casing made of a deformable material such as synthetic rubber in order to provide shock absorption to the monitoring device and/or provide for a more snug fit of the monitoring device 230 once installed with respect to the hollow portion 220.

Figure 9:
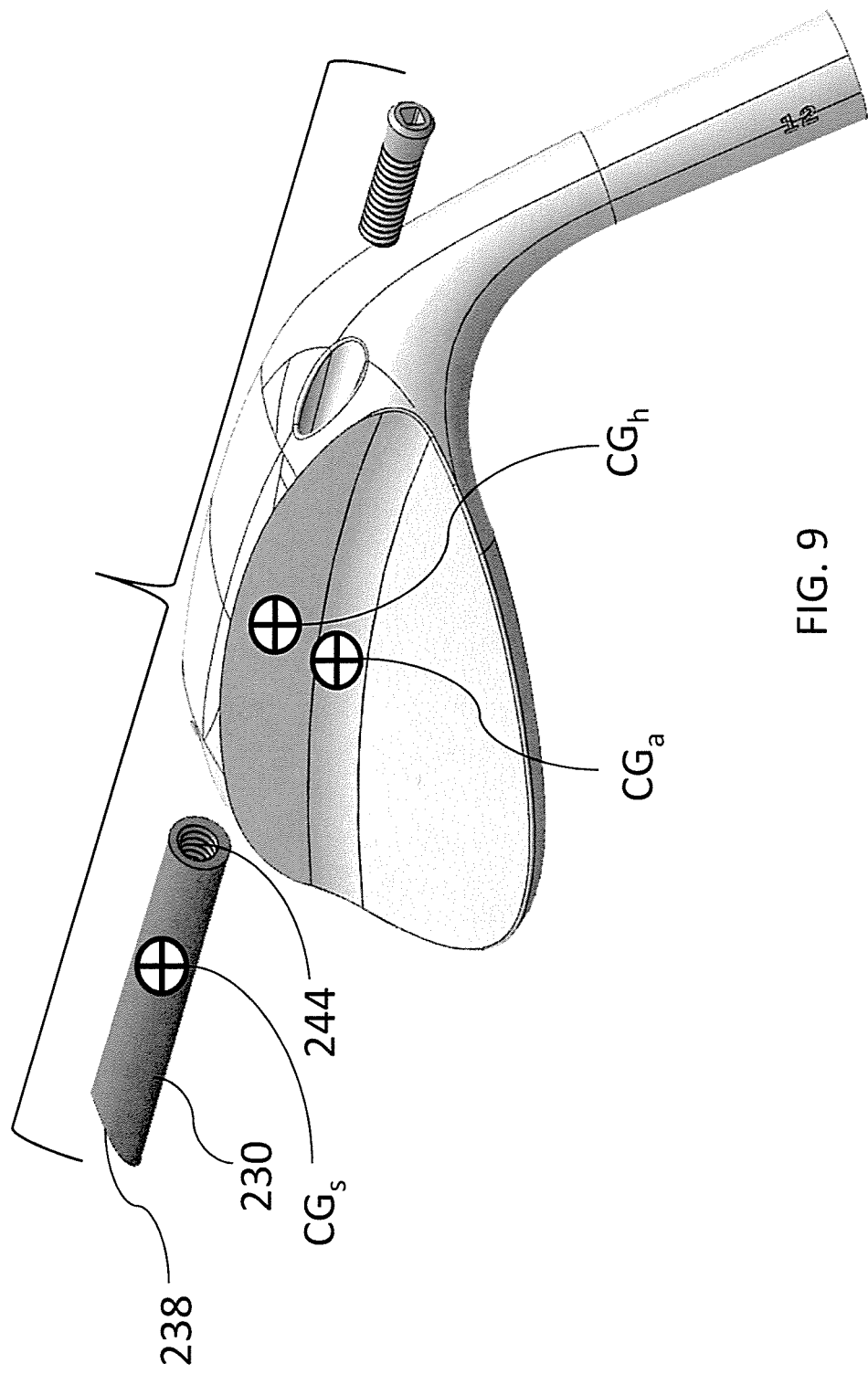
FIG. 9 is an exploded view of a sporting apparatus and a monitoring device of the present disclosure illustrating various centers of gravity for the monitoring device and the sporting apparatus.

In another aspect, as illustrated in FIGS. 9 and 11, the monitoring device 230 may comprise a monitoring device center of gravity $CG_s$, and the golf club head 212 may also comprise a virtual center of gravity $CG_h$ (the virtual center of gravity comprising where the center of gravity would have been located with the hypothetical plug of material 226 in place). The golf club head 212 may also have an actual center of gravity, $CG_a$ somewhat offset from the virtual center of gravity $CG_h$ (also known herein as the hypothetical center of gravity) by virtue of the hypothetical plug of material 226 having been removed from the golf club head 212. In this aspect, as illustrated in FIG. 11, the monitoring device center of gravity $CG_s$ may be configured such that when the monitoring device 230 is installed in the golf club head 212, it substantially aligns with the virtual center of gravity or actual center of gravity. Thus, when $M_1=M_2$, and $CG_s$ is substantially aligned with $CG_h$, the golf club head 212 with the monitoring device 230 installed may have neither its mass nor its center of gravity affected by the monitoring device 230. This may contribute to more accurate swing analysis.

In a preferred aspect, the monitoring device may be configured with two ends 238, 240 one or both of which may compliment the contours of the golf club head 212 proximate the ends 238 and/or 240. This is best illustrated by the hypothetical plug of material 226 of FIG. 2, showing a hypothetical first end 238a exhibiting a contour similar to and/or substantially complimentary of the toe region 222 golf club head 212 and a hypothetical second end 240a exhibiting a contour similar to and/or substantially complimentary of the heel region 224. Such a complimentary contour is also illustrated by end 238 of FIGS. 1, 10, and 11.

In a preferred aspect, either or both ends 238, 240 of the monitoring device, may be threaded or otherwise configured to permit the monitoring device 230 to be retained within the hollow portion 220 with a securing structure. For example, a threaded bolt or screw 242 may pass through one or more threaded or unthreaded retention flanges 243, and thread into a female threaded region 244 (best seen in FIGS. 9 and 11) end 240 of the monitoring device to permit the monitoring device 230 to be removeably secured within the golf club head 212.

Alternative exemplary securing structures configured to secure the monitoring device 230 within the hollow portion 220 are illustrated in FIGS. 4-7 and 4a-7a. In these examples, monitoring devices, generally 400, 500, 600, and 700, may each have a first end 430, 530, 630, and 730, respectively, the term "end" in this context including but not limited to the literal left end of the monitoring device, and also including some or all of that portion of the monitoring device to the left of about the midline "M" thereof. The first end 430, 530, 630, and 730, may be configured with a first securing structure which may comprise, for example, an internally threaded portion 444, 544, 644, and 744, respectively, for receiving a threaded bolt or other fastener to secure the respective monitoring devices 400, 500, 600, and 700 within a golf club head as previously described. Alternatively, as will now be readily appreciated, the first end 430, 530, 630, and 730 may, rather than comprising internally threaded portions, comprise an externally threaded portion (not shown) to be threadably received within complimentary internal threads within the hollow portion 220.

Each monitoring device 400, 500, 600, and 700 may further comprise a second end 440, 540, 640, and 740, the term "end" in this context, including but not limited to, the literal right end of the monitoring device, and also including some portion or the entire portion of the monitoring device to the right of about the midline "M" thereof. As illustrated, the second end 440, 540, 640, and 740 may be generally opposite the first end, 430, 530, 630, and 730, and may be configured with a second securing structure as will now be described.

As illustrated in the example of FIGS. 4 and 4a, the second securing structure may comprise an o-ring 450, which may be made of a deformable material. The o-ring 450 may be configured to be received within a complimentary groove in the monitoring device 400 and/or within the inner wall of the hollow portion 220 upon installation of the monitoring device 400. The o-ring 450 may assist in securing the second end 440 of the monitoring device 400 within the hollow portion, while a threaded bolt or other fastener may secure the first end 430 thereof upon being threaded and tightened within the internally threaded portion 444. In an alternative aspect, the o-ring 450 may comprise a non-resilient member or stop that may circumnavigate the second end 440 or may go around only a portion thereof, and may engage a flange or opposing stop formed on the inner wall of the hollow portion, which opposing stop may, for example, comprise a flange that circumnavigates the inner wall of the hollow portion or may go around only a portion thereof.

The second securing structure may alternatively or additionally comprise a flange, wedge, or other structure configured to mate with or slide within a complimentary groove, slot, or other recess in the inner wall of the hollow portion 220 upon installation of the monitoring device 500. As illustrated in the example of FIGS. 5 and 5a, the second securing structure may comprise a wedge-shaped structure 550 that may be slideably received within a complimentary shaped slot, groove, or recess in the inner wall of the hollow portion 220 upon installation of the monitoring device 500. A secure fit of the monitoring device 500 on both ends thereof within the golf club head may be achieved, for example, by tightening a bolt into the internally threaded portion 544, which may draw the second end 540 of the monitoring device 500 into friction fit or locking engagement with the inner wall of the hollow portion 220. In this aspect, the second securing structure and complimentary shaped slot, groove, or recess in the inner wall of the hollow portion 220 may function, in addition to comprising a securing structure, as an alignment structure or key, enabling the monitoring device 500 to be mounted and retained in the golf club head in a particular orientation, for example, to permit an outer end 560 of the monitoring device 500 to be contoured to match the contour of the golf club head, such as the heel portion 260 or toe portion 262 thereof.

The second securing structure may alternatively or additionally comprise a configuration similar to the wedge-shaped structure 550 described with respect to FIGS. 5 and 5a, for example, a frustum-type configuration as illustrated with respect to monitoring device 600 in FIGS. 6 and 6a. In this aspect, the monitoring device 600 may comprise a first end 630 that may be configured substantially as previously described, and may have a second end 640 that may in whole or in part comprise a frustum 650. In the example illustrated in FIGS. 6 and 6a a semi-conical frustum, i.e., a frustum comprising an elliptic cone portion or an oval cone portion may be used. Other shapes, however, such as a true conical frustum, also termed a "frustoconical" configuration, a square frustum, or a pentagonal frustum, etc., may also be used. It may be desirable, when a frustum or otherwise symmetrical configuration is used for the second end 640, to include a key 642 or other similar component configured to align the monitoring device 600 within a keyed slot in the hollow portion 220 in a particular orientation within the hollow portion 220, in order to take advantage of a complimentary contour feature of the monitoring device ends and the golf club contour as will subsequently be described. As will be readily appreciated, the key 642 may alternatively be positioned within the hollow portion 220 and the corresponding slot positioned within the second end 640 of the monitoring device 600. Although only one key 642 is illustrated, a plurality of such components may of course be used.

When the monitoring device 600 comprises a frustum, or at least a portion thereof comprises a frustum, as will now be appreciated, the second end 640 may be configured to "nest" within a complimentary shaped portion of the hollow portion 220. Such nesting may result in a friction fit or other clamping engagement, thereby securing the second end 640 within the hollow portion 220, for example, when a fastener such as a bolt or screw thread is tightened relative to the first end 630.

As illustrated in FIG. 6a, the monitoring device 600 first end 630 may have an outer end 635 comprising an elliptical or oval shape when viewed head-on. Such shape may be the result of the first end 630 having a cross section of that shape. Such cross section may thus comprise a true vertical cross section, i.e., along lines 6A-6B. Alternatively, the elliptical or oval shape or other non-round shape of the outer end 635 may be the result of the outer end 635 having a contour as illustrated by the dotted line 635a of FIG. 6, intended to illustrate a contour that might compliment the contour of an outer surface of a golf club head, such as a heel end thereof.

Similarly, as illustrated in FIG. 6a, the monitoring device 600 second end 640 may have an outer end 660 that may have an elliptical or oval shape when viewed head-on. Such shape may be the result of the second end 640 having a cross section of that shape. Such cross section may thus comprise a true vertical cross section, i.e., along lines 6C-6D. Alternatively, the elliptical or oval shape or other non-round shape of the outer end 660 may be the result of the outer end 660 having a contour as illustrated by the dotted line 660a of FIG. 6, intended to illustrate a contour that might compliment the contour of an outer surface of a golf club head, such as a toe end thereof.

It will also be appreciated that the hollow portion and any of the monitoring device configurations described herein may have an asymmetrical cross section, or a cross section of partial asymmetry, such as a tear drop, non-equilateral triangle, etc., requiring installation of the monitoring device in only one orientation, which may be convenient, for example, in the case of a monitoring device having one or more ends having a contour that complement the region of the hollow portion proximate the golf club head, as previously described.

As illustrated in FIGS. 7 and 7a, the second end securing structure may comprise an external threaded section 750. In this aspect, the external threaded section 750 may permit the monitoring device 700 to be threadably engaged by complimentary internal threads within the hollow portion 220. In an alternative aspect, both the second end 740 and the first end 730 of the monitoring device may comprise an external threaded section 750, or the external threaded section may run substantially the entire length of the monitoring device 700, potentially eliminating the need for the internally threaded portion 744 and a bolt or screw to secure the first end 730 within the hollow portion 220.

As further illustrated in FIGS. 7 and 7a, the monitoring device 700 may comprise a monitoring device end 760 having a key, slot, groove, square or other multisided hole or other recess or protuberance configured to engage a tool to install the monitoring device 700 in the hollow portion 220. In this example, the monitoring device end 760 comprises a Phillips head slot 765.

Figure 8:
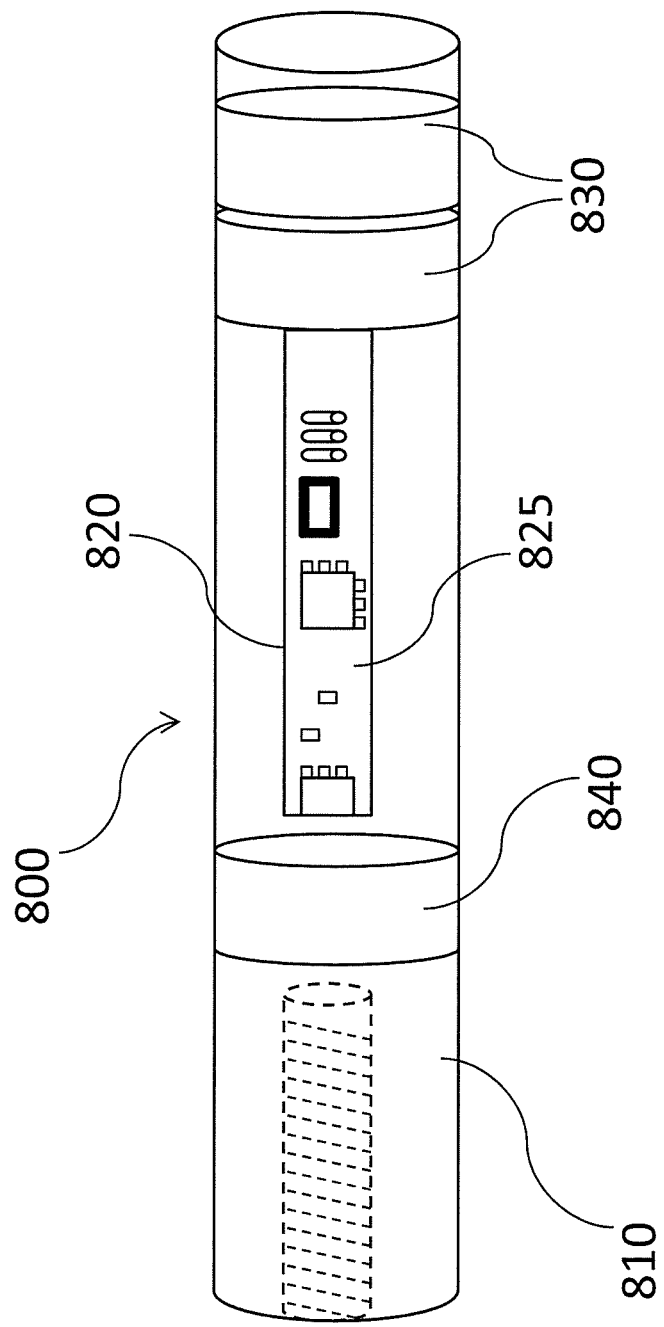
FIG. 8 is another schematic illustration of an exemplary monitoring device of the present disclosure.

Referring now to FIG. 8, there is illustrated an example of how a monitoring device, generally 800, may be configured according to certain aspects described herein. The monitoring device 800 may comprise an outer casing 810 that may have a generally cylindrical shape as illustrated, or any other convenient shape. The outer casing may be fabricated of any material suitable for the purpose, including without limitation, plastic, rubber, synthetic rubber, metal, resin, composite, etc. In a preferred aspect, the outer casing 810 may be fabricated of a shock absorbing material, such as a deformable polymer, in order to permit the electronic components of the monitoring device 800 to withstand the shock and vibrations of a ball strike when a golf club head in which the monitoring device 800 is installed, and/or to more readily enable the monitoring device 800 to be secured within the golf club head, i.e., with a friction fit, as previously described.

The monitoring device 800 may comprise a sensor component 820, which may comprise, for example, a circuit board 825 onto which one or more subcomponents, such as microprocessors, transmitters, accelerometers, resistors, capacitors, etc., may be mounted, arranged and connected. Such sensor component 820 may, for example, be of the type commercially available and employed in the shaft-mounted Swingbyte SB2 clip-on type sensor.

As further illustrated, the monitoring device 800 may comprise one or more batteries 830 for powering the monitoring device's electronic components. In one aspect, the batteries 830 may comprise a configuration complimentary to the inner contours of the outer casing 810 of the monitoring device 800, in this case, generally cylindrical. Such batteries 830 may, for example, comprise a configuration similar to watch batteries. Other battery types and configurations are of course possible, provided they provide sufficient power to power the sensor component 820, and have a size capable of being fitted within the outer casing 810. In an alternative aspect, the battery(ies) may be positioned within the shaft or grip of the golf club and connected to the monitoring device 800, such as with wiring.

The monitoring device 800 may further comprise one or more weights 840, for purposes of giving the monitoring device substantially the same mass as the theoretical amount of golf club head material lost to achieve the hollow portion 220, for example the hypothetical plug of material 226. The battery(ies) 830 may comprise one or more weights for the same purpose. The mass of theoretical amount of golf club head material lost to achieve the hollow portion (i.e., a void) may be called a hypothetical mass, which may be the mass of the hypothetical plug of material 226 and determined by multiplying the volume of the golf club head material lost by the density of the material lost. Additionally or alternatively, the outer casing 810 may be fabricated of sufficiently dense material to provide the same amount of needed mass. Stated otherwise, the monitoring device 800 may be configured with sufficient mass to provide a golf club head into which the monitoring device 800 is secured substantially the same weight as a comparable golf club head without a monitoring device 800 and without a hollow, void, or recess for securing such a monitoring device (i.e., a stock golf club head).

In a preferred aspect of the disclosure, a monitoring device such as those illustrated and described herein may be configured to compensate for post impact vibrations to the golf club head. In a golf club head comprising a monitoring device, the monitoring device may be configured to transmit data responsive to a pre-impact swing path of the golf club head, to disregard or "trim" data responsive to a post-impact swing path, and to determine a hypothetical post-impact swing path based at least in part on at least a portion of the pre-impact swing path.

Figure 12:
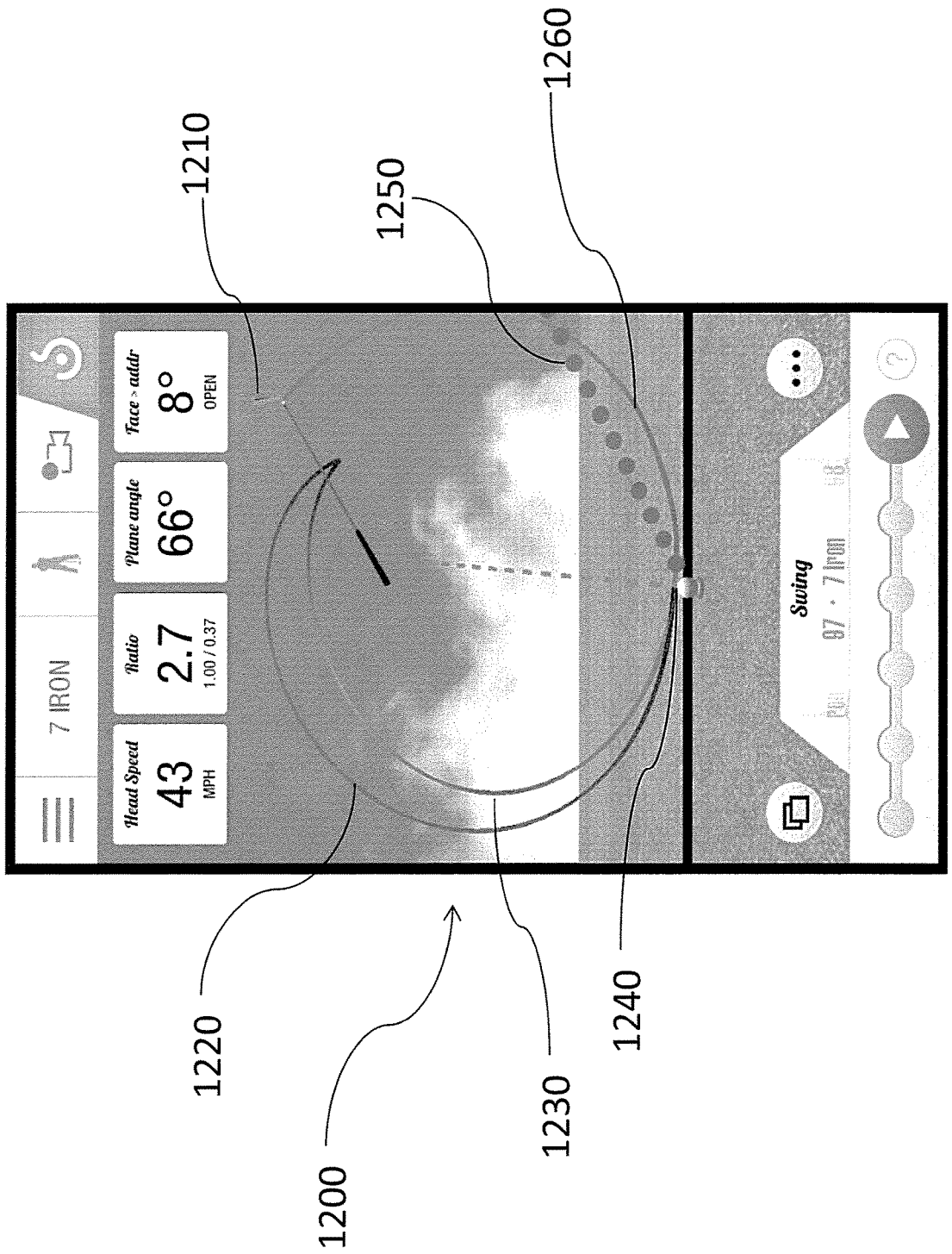
FIG. 12 is a schematic illustration of a graphic display of a swing path for a sporting apparatus such as a golf club.

Referring now to FIG. 12, there is illustrated a graphic display, generally 1200, for a golf club swing path, such as achieved using a Swingbyte SB2-type sensor clamped or adhered to a golf club shaft as illustrated in FIG. 1. Such graphic display 1200 may be displayed on a remote device, such as a handheld device, i.e., a smart phone; a portable device, such as a tablet computer; or on a desktop device, such as a computer terminal. Such graphic display may be achieved using components, algorithms and software embedded in the shaft-mounted monitoring device and/or the remote device, as described in U.S. Pat. No. 8,696,482.

The monitoring device may comprise a transmitter configured to transmit data specific to the swing path to the remote device for processing and displaying as the graphic display 1200. As illustrated, the graphic display 1200 may display a virtual golf club 1210 in one or more swing positions, in this example, at the follow through position proximate the conclusion of a golf swing. As further illustrated, the graphic display 1200 may display a swing path as recorded, sensed, and/or transmitted by the shaft-mounted monitoring device. Such swing path as displayed may comprise a pre-impact backswing path 1220, and a pre-impact downswing path 1230, prior to the point of impact with a golf ball 1240. The graphic display may further display a hypothetical post impact golf ball path 1250 and a post-impact swing path 1260. Because, in this example, the monitoring device is mounted to the shaft of the golf club, or even the grip, the post-impact swing path remains relatively unaffected by post-impact vibrations experienced at the point of impact, i.e., the golf club head.

Figure 13:
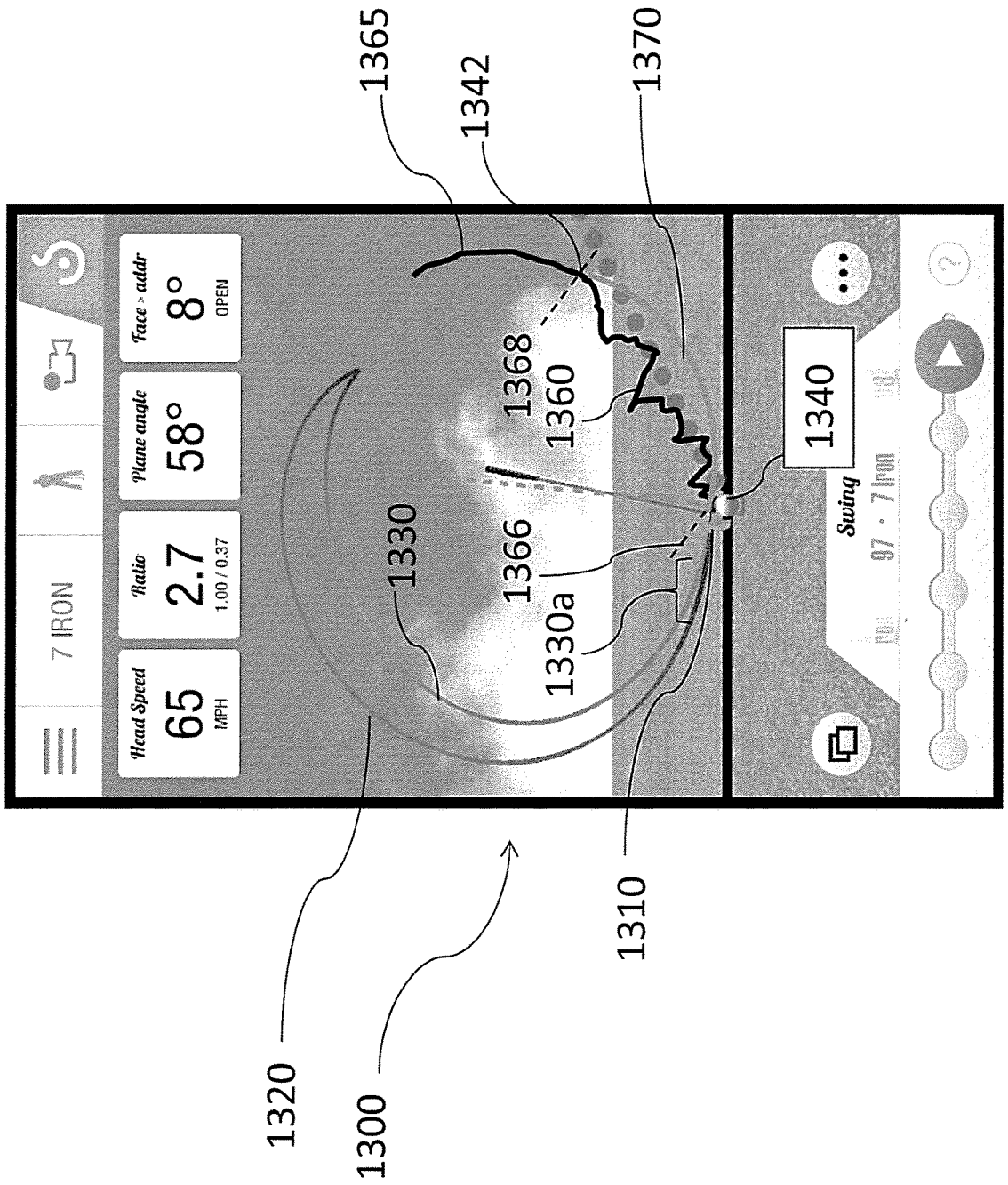
FIG. 13 is a schematic illustration of a graphic display of a swing path for a sporting apparatus such as a golf club illustrating post impact swing path anomalies and correction therefore according to the teachings of the present disclosure.

Referring now to FIG. 13, there is illustrated a schematic graphic display, generally 1300, displaying a virtual golf club head 1310 at the point of impact. The display 1300 illustrated in FIG. 13 is intended to illustrate recorded swing paths such as might be experienced in mounting a monitoring device of the prior art within a golf club head. As there illustrated, a monitoring device mounted in the virtual golf club head 1310 may result in a fairly reliable recording and display of the backswing (i.e. pre-impact swing path 1320) and the downswing (i.e., pre-impact swing path 1330) although as previously indicated, there may be some head wobble during the backswing and downswing, but not nearly as much as occurs post impact. As illustrated, at the point of impact with the golf ball 1340, due to the massive vibrations to the virtual golf club head 1310, particularly in the case of an off-center hit, the post-impact swing path 1360 may be sporadic and of relatively little practical use from the point of impact with the golf ball 1340 until sometime thereafter, illustrated as point 1342, where post-impact vibrations of the virtual golf club head 1310 have substantially ceased, to the point where the post-vibration post-impact swing path 1365 may be more effectively recorded and displayed for effective use.

Figure 14:
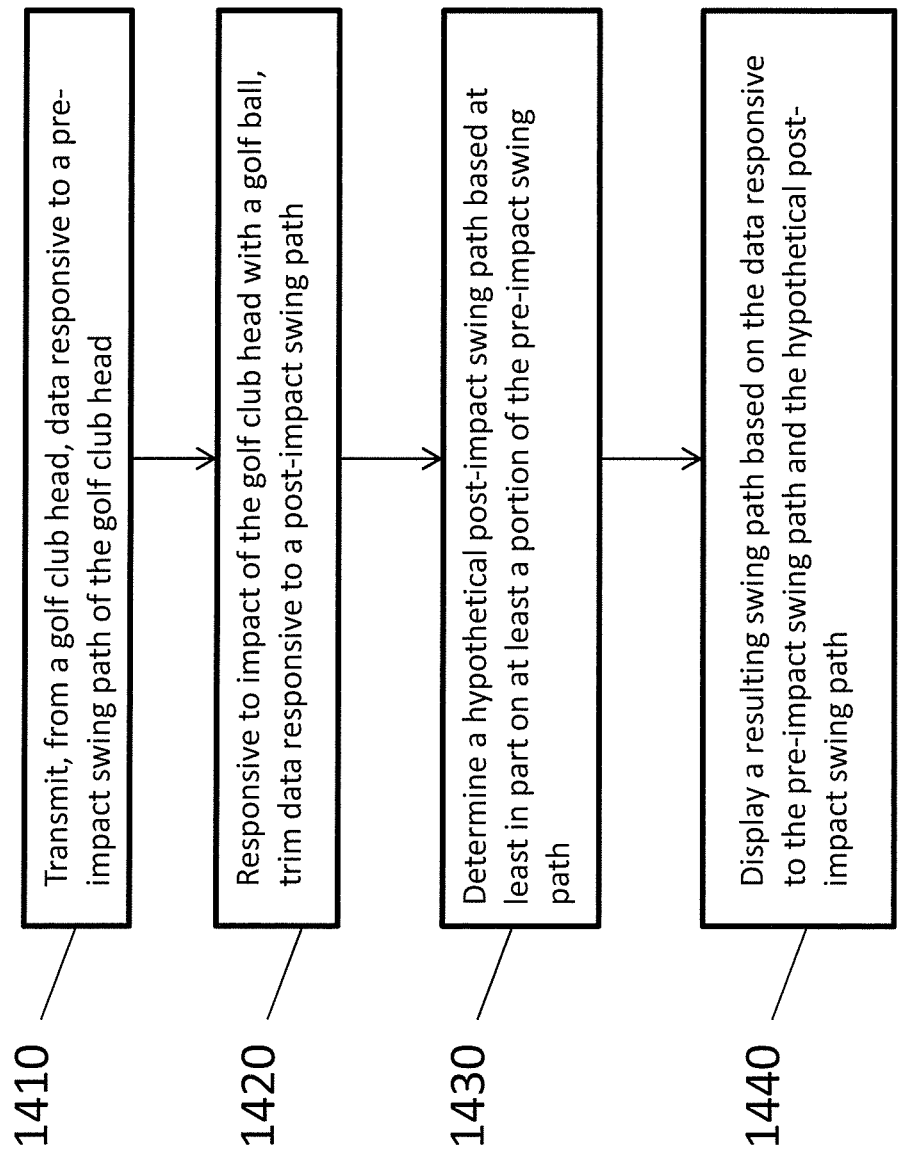
FIG. 14 is a flow chart illustrating an exemplary method of the present disclosure.

In a preferred aspect of the disclosure, the monitoring device (or remote device associated therewith) may be configured to trim data from the post-impact swing path with the golf ball 1340, to avoid the undesirable post-impact data, represented schematically as post-impact swing path 1360. Referring now to FIG. 14, there is illustrated a flow chart providing one way in which a monitoring device such as described herein may be configured, at operation 1410, to transmit data associated with a path of the golf club head. The monitoring device may, at operation 1420, disregard or "trim" data responsive to a post-impact swing path, illustrated schematically in FIG. 13 as "trim" lines 1366, 1368 relative to post-impact swing path 1360. Trimming data, as discussed herein, may refer to excluding some of the extreme data values, a process called truncation. This is generally done to obtain a more robust estimation, and the extreme values are considered outliers. Any number of techniques may be used to trim data, such as the trimmed mean, modified mean, interquartile mean, midhinge, interdecile range, or interquartile range, among other techniques.

At operation 1430, a hypothetical post-impact swing path, illustrated in FIG. 13 as 1370, may be determined based at least in part on at least a portion of data associated with a pre-impact swing path (i.e., data with regard to the pre-impact swing path 1330 or pre-impact swing path 1320). As illustrated, this determination may be made, for example, by extrapolating the hypothetical post-impact swing path 1370 from data associated with a portion 1330a of the pre-impact swing path 1330 proximate the point of impact, the golf ball 1340. As further illustrated in FIG. 13, the hypothetical post-impact swing path 1370 may be displayed on the display 1300, and the "trimmed" data for the post-impact swing path 1360 may be either displayed or not displayed. Data for the post-impact swing path 1360 (i.e., data of an "actual" post-impact swing path) may be considered data captured directly by one or more sensors in a monitoring device or data not adjusted to consider substantial impact related effects to the golf club head. As also illustrated, the display may "join" the hypothetical post-impact swing path 1370 with the post-vibration post-impact swing path 1365 to display an approximation of the actual swing path corrected for post-impact vibrations of the club head. At operation 1440, a resulting swing path based on the data associated with the pre-impact swing path and the hypothetical post-impact swing path may thus be displayed on the display 1300.

In another aspect of the disclosure, the hypothetical post-impact swing path 1370 may be determined at least in part by the data associated with post-vibration post-impact swing path 1365. In this aspect, the post-vibration post-impact swing path 1365 or a portion thereof may be extrapolated "backwards" (or interpolated) to create the hypothetical post-impact swing path 1370 or a portion thereof. In still another aspect, both the pre-impact swing path 1330 and the post-vibration post-impact swing path 1365, or portions thereof, may be extrapolated to create the hypothetical post-impact swing path 1370. In one aspect, such extrapolations may be performed from both ends, represented by "trim" lines 1366, 1368, with the effective resulting hypothetical post-impact swing path 1370 meeting in the middle or substantially in the middle of the two "trim" lines 1366, 1368.

In yet another aspect of the disclosure, the monitoring device 230 may be configured to store and/or transmit data from several practice swings, i.e., swings without a golf ball impact, and use such stored and/or transmitted data to "normalize" or otherwise adjust the post-impact swing path 1360 and create the hypothetical post-impact swing path 1370. In yet another aspect, the monitoring device 230 may be configured to store and/or transmit data from multiple swings with a golf ball impact, and sum, average, or otherwise use such stored and/or transmitted data from multiple swings to adjust the post-impact swing path 1360 and create the hypothetical post-impact swing path 1370. In this aspect, two or three such swings may be sufficient to secure reliable results.

Figure 15:
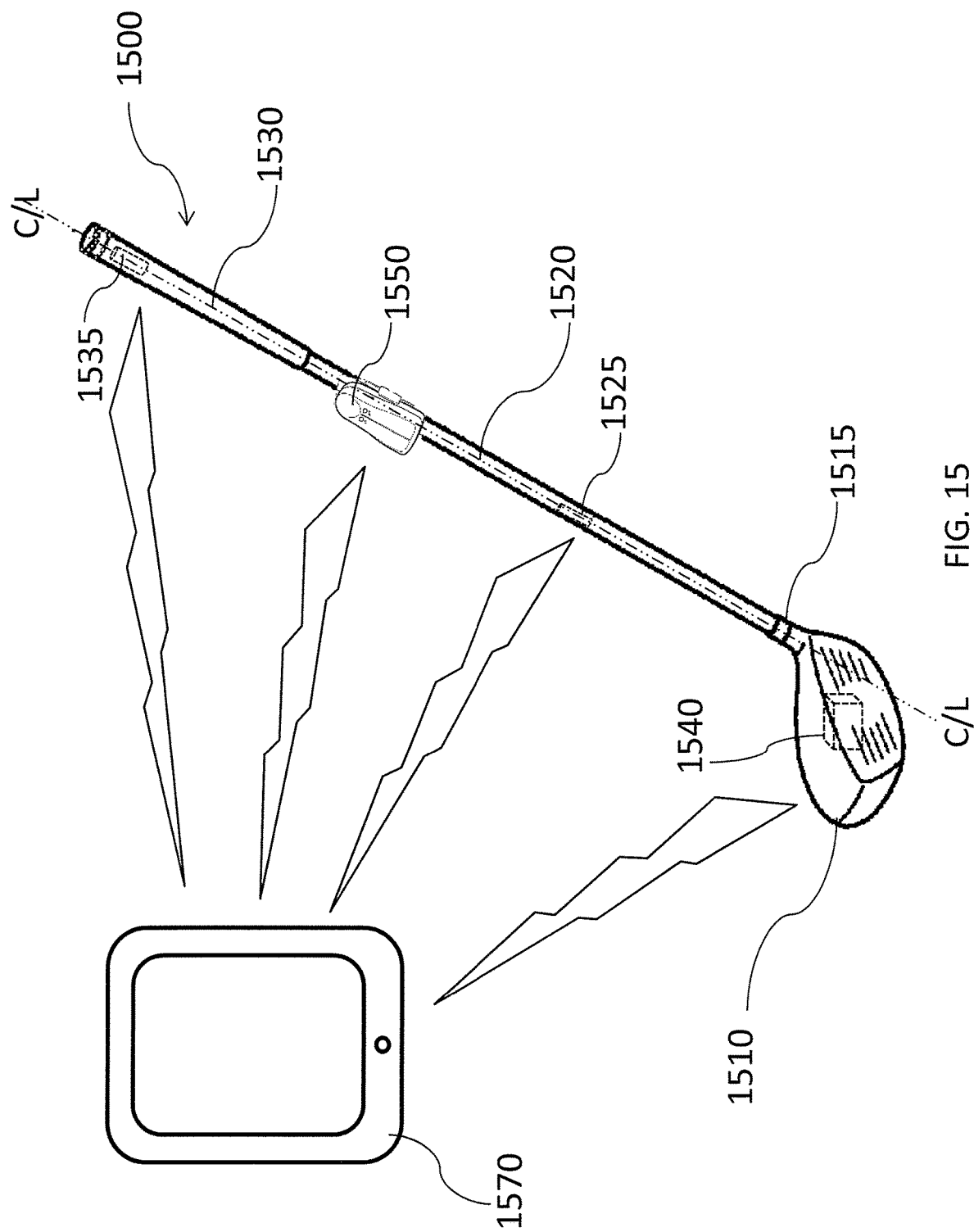
FIG. 15 is a schematic illustration of a system of the present disclosure comprising a sporting apparatus configured with multiple monitoring devices in communication with a remote device.
Figure 16:
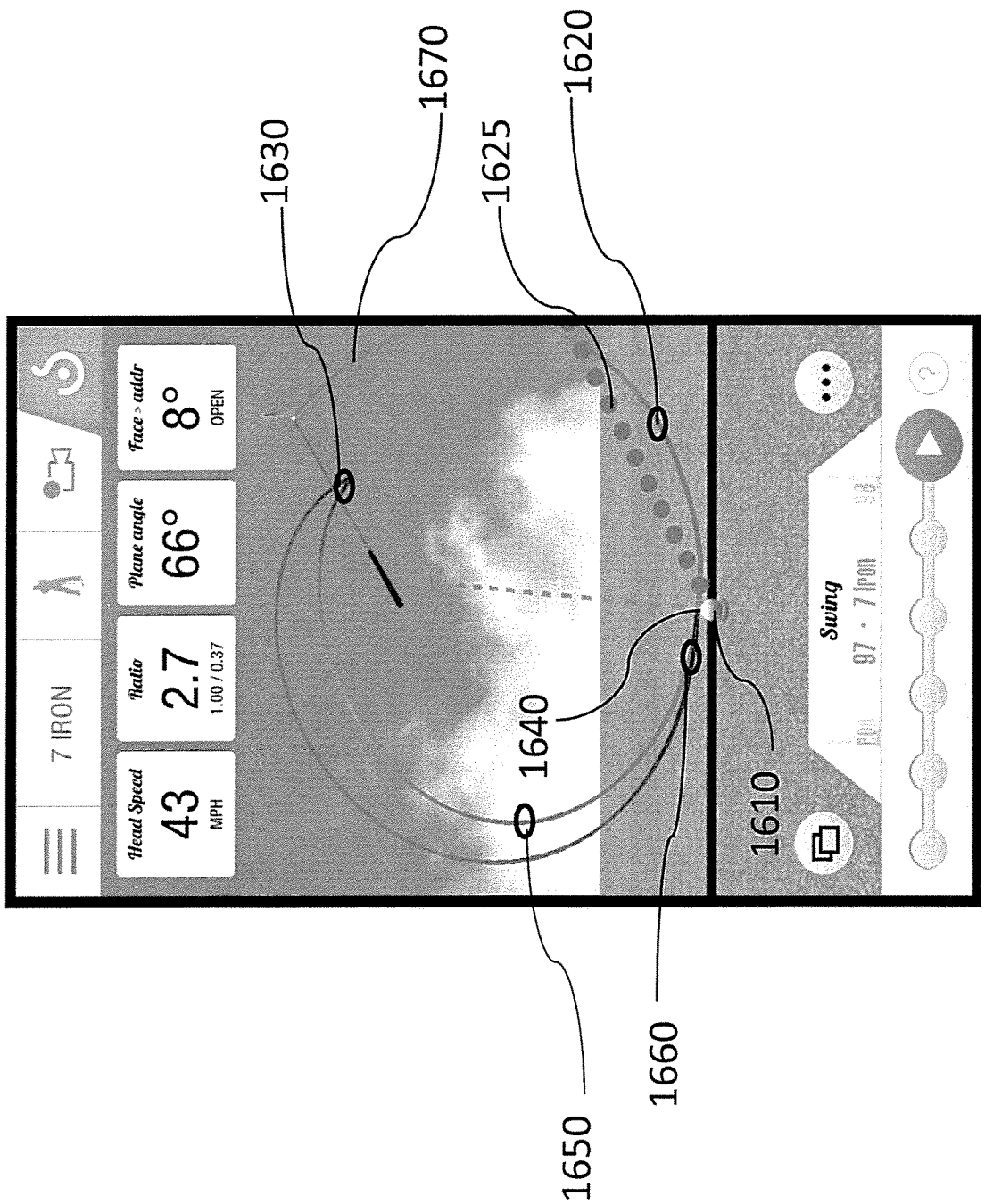
FIG. 16 is a schematic illustration of a graphic display of a swing path for a sporting apparatus such as a golf club illustrating an aspect of the disclosure in which multiple monitoring devices may be used, for example, at different portions of the swing path.

Another aspect of the disclosure is a system illustrated in FIG. 15. In this aspect, a golf club, generally 1500, comprising a golf club head 1510 connected via a hosel 1515 to a shaft 1520 having a grip 1530 may be provided with a monitoring device 1540 in the head, substantially as described herein or as described, as another example, in U.S. Patent Application Publication No. US 2013/0267338 A1. In this aspect, the golf club 1500 may additionally comprise a monitoring device 1550, that may, for example, be attached to the shaft 1520, and exhibit substantially the same functionality as the monitoring device 1540, in terms of sensing motion of the golf club 1500 and processing, storing, and transmitting data pertaining thereto. The monitoring devices 1540, 1550 may communicate with and/or be used in conjunction with a remote apparatus 1570 such as a computer tablet, smart phone, laptop computer, etc. In this aspect, the monitoring device 1540, monitoring device 1550, and/or related remote apparatus 1570 may be configured to receive, process, transmit, and/or display only the best data available from the monitoring device 1540 and monitoring device 1550. For example, referring now to FIG. 16, the monitoring device 1540 may be used at all times during the swing except from the point of impact of the golf club head 1510 with a ball 1610 until a point 1620 at which the vibration of the golf club head 1510 post impact substantially ceases, and/or except at the top 1630 of the backswing, where the golf club head experiences "wobble." In the context of the previous example, the monitoring device 1550 may be used at times during the swing when monitoring device 1540 is not used (i.e., at impact or at the top of the backswing).

As another example, the golf club 1500 may have additional monitoring devices, such as a monitoring device 1525 within the shaft 1520 and/or a monitoring device 1535 within the grip 1530, to provide multiple opportunities to capture the most accurate readings from multiple parts of the swing. As illustrated, the plurality of monitoring devices 1525, 1535, 1540, 1550 may be relatively evenly spaced along the golf club 1500, for example, generally along the longitudinal axis or center line C/L of the sporting apparatus handle, shaft, hosel, etc. Other numbers of monitoring devices and spacing and monitoring device securing arrangements are of course contemplated herein.

The plurality of monitoring devices 1525, 1535, 1540, 1550 may cooperate to determine the most accurate and/or relevant swing path data depending on which of the plurality of monitoring devices 1525, 1535, 1540, 1550 is capturing the most accurate and/or relevant data at various positions of the swing being analyzed. Referring again to FIG. 16, if it is known (or determined by the system), for example, in the case of a golf club 1500 swing, that the monitoring device 1540 provides the most accurate/relevant swing data from the point of takeaway 1640 to just before the top 1630 of the backswing and from a point just prior to the point of impact of ball 1610, that monitoring device may only have its data used for those two portions of the swing. If it is further known, for example, that the monitoring device 1535 provides the most accurate/relevant swing data from the top 1630 of the backswing to an intermediate point 1650, for example, around the point where the golf club 1500 is parallel to the ground on the downswing, that monitoring device may only have its data used for that portion of the swing. Similarly, if the monitoring device 1550 provides the most accurate/relevant swing data from the intermediate point 1650 to the point 1660 just prior to the point of impact with the ball 1610, that monitoring device may only have its data used for that portion of the swing. And if it is further known, for example, that the monitoring device 1525 provides the most accurate/relevant swing data from the point of impact with the ball 1610 through the rest of the golf swing 1670 (i.e., follow through), that monitoring device may only have its data used for that portion of the swing.

Two or more of the plurality of monitoring devices 1525, 1535, 1540, 1550 may communicate with a computing device, such as remote apparatus 1570, any one of the other monitoring devices, or any other device, configured to perform, for example, an intermediate step of calculation and sorting that makes sense of data from the plurality of monitoring devices 1525, 1535, 1540, 1550 in order to have their respective swing data captured, compared, trimmed, normalized, and/or aggregated in order to create an integrated set of data representative of the best available data for the swing being analyzed.

Figure 17:
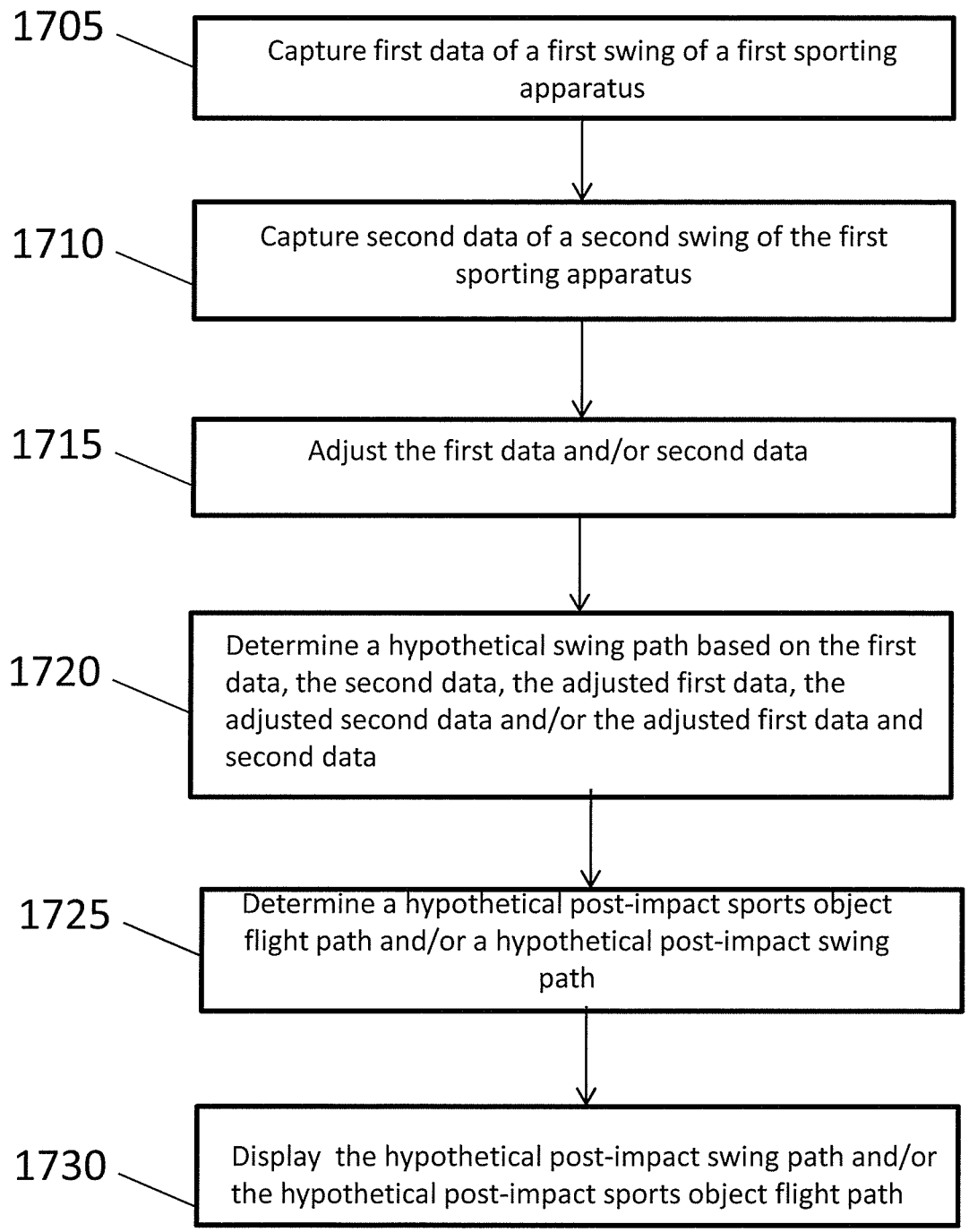
FIG. 17 is a flow chart illustrating an exemplary method of the present disclosure.

FIG. 17 illustrates an exemplary method for determining a swing path. At operation 1705, a first data of a first swing of a first sporting apparatus is captured. The first data may be from one or more devices, such as remote apparatus 1570, monitoring devices 1525, 1535, 1540, or 1550, or the like. The first swing may be a non-impact swing (for example, a swing without an impact with a second sporting apparatus) or an impact swing (for example, a swing that the first sporting apparatus impacts a second sporting apparatus). At operation 1710, a second data of a second swing of the first sporting apparatus is captured. The second swing may be a non-impact or impact swing. The time between the first swing and the second swing may be within a short stretch of time, such as seconds or minutes, or within a long stretch of time, such as hours, days, or weeks.

At operation 1715, the first data and/or second data may be adjusted. The first data and/or second data may be adjusted by trimming, normalizing, or another statistical based method or non-statistical based method in order to assist in determining a swing path that may include a pre-impact path or a post-impact path. In an example, when there is a non-impact swing, the remote apparatus 1570 or one or more of the monitoring devices 1525, 1535, 1540, or 1550 (separately or together) may delineate data from a pre-impact swing path and data from a post-impact swing path based on an estimation of a hypothetical point of impact of a ball (since there is no impact of a ball in a non-impact swing). In this example, after the data of the pre-impact swing path and post-impact swing path have been determined, then the post-impact swing path may be trimmed and normalized.

At operation 1720, a hypothetical swing path (i.e., hypothetical post-impact swing path and/or the hypothetical pre-impact swing path) for the first swing or the second swing may be determined based on the first data, the second data, the adjusted first data, and/or the adjusted second data. At operation 1725, hypothetical post-impact flight path (i.e., ball path 1625) of a sporting object (i.e., the ball 1610) may be determined based on the first data, the second data, the adjusted first data, and/or the adjusted second data. For example, a trimmed and/or normalized post-impact swing path or pre-impact swing path may be used in the determination of the flight of the ball 1610 or a hypothetical ball (for example in the situation of a non-impact swing). At operation 1730, the hypothetical post-impact swing path and/or the post-impact sports object flight path may be displayed as in shown in FIG. 16, for example. The operations of FIG. 17 and other methods discussed herein may be performed on a single device or distributed over multiple devices. Although several operations are discussed herein, it is understood that one or more operations may be removed or performed in any reasonable order.

In another aspect, a system of the present disclosure may comprise a plurality of sporting apparatus, for example, a golf glove with a monitoring device therein, an arm band with a monitoring device therein, and/or a golf club with one or more monitoring devices therein, each monitoring device being configured to monitor a user's motion, such as a golf swing, the system being configured to pick and choose among the various monitoring devices which of them is, at any point during the motion being monitored, which monitoring device is transmitting the most accurate and/or relevant motion data, the system being further configured to process and accumulate (or sum) such data to result in a display of the user's path of motion being monitored.

Figure 18:
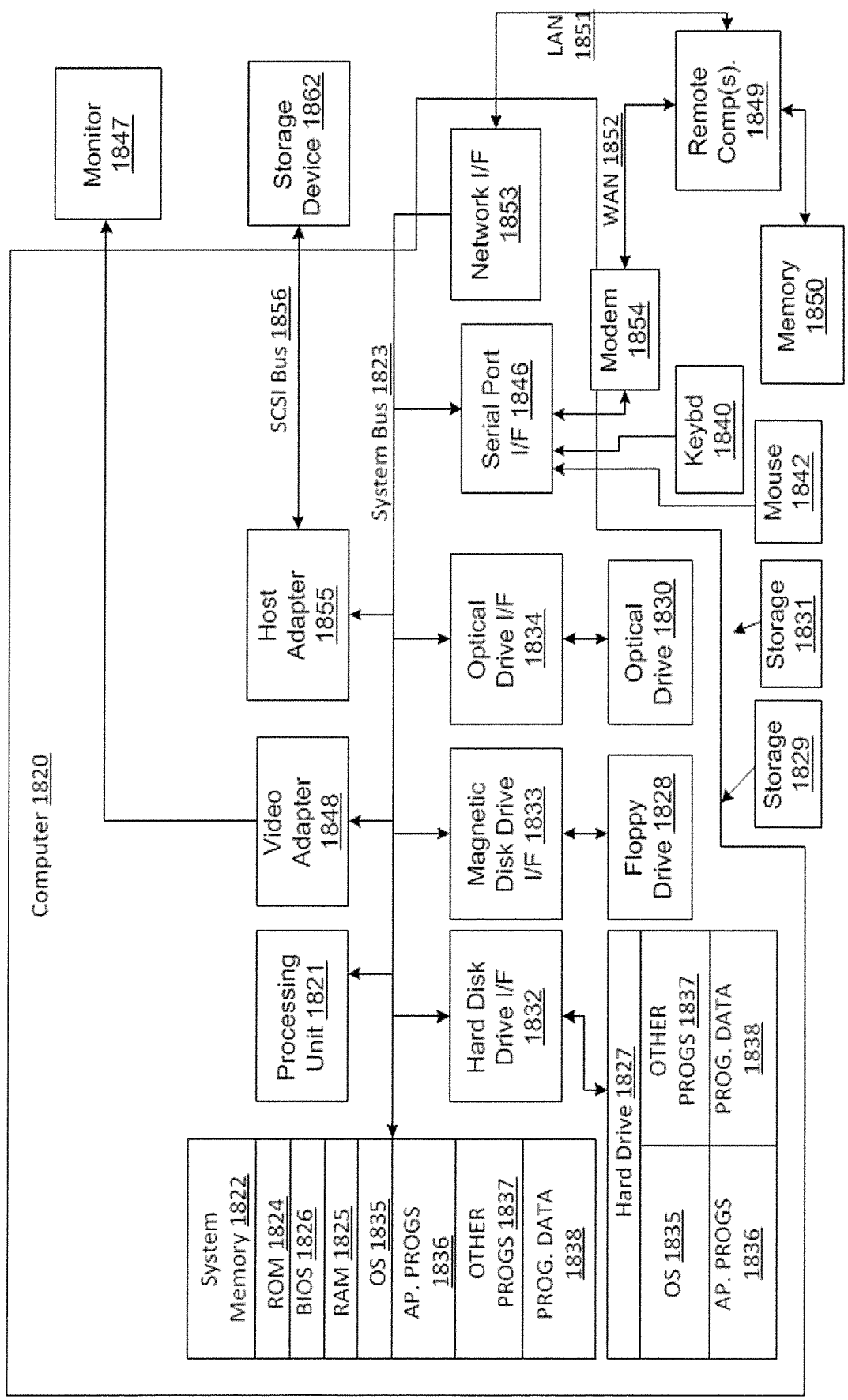
FIG. 18 is an exemplary block diagram representing a computer system in which aspects of the methods and systems disclosed herein or portions thereof may be incorporated.

FIG. 18 and the following discussion are intended to provide a brief general description of a suitable computing system in which the methods and systems disclosed herein and/or portions thereof may be implemented. Although not required, the methods and systems disclosed herein are described in the general context of computer-executable instructions, such as program modules, being executed by a computing system. Generally, program modules include routines, programs, objects, components, data structures and the like that perform particular tasks or implement particular abstract data types. It should be appreciated the methods and systems disclosed herein or portions thereof may be practiced with computer system configurations, including a client workstation, server, hand-held device, multi-processor system, microprocessor-based or programmable consumer electronic, network PC, minicomputer, mainframe computer, and the like. The methods and systems may also be practiced in distributed computing environments where tasks are performed by remote processing devices that are linked through a communications network. In a distributed computing environment, program modules may be located in both local and remote memory storage devices.

FIG. 18 is a block diagram representing a general purpose computer system in which aspects of the methods and systems disclosed herein or portions thereof may be incorporated. The monitoring devices (i.e., the monitoring device 230, 400, 500, 600, 700, and 800, etc.), the remote apparatus 1570, among other devices may include one or more of the components of computing device 1820 as described herein. As shown, the exemplary general purpose computing system includes a computer 1820 or the like, including a processing unit 1821, a system memory 1822, and a system bus 1823 that couples various system components including the system memory to the processing unit 1821. The system bus 1823 may be any of several types of bus structures including a memory bus or memory controller, a peripheral bus, and a local bus using any of a variety of bus architectures. The system memory includes read-only memory (ROM) 1824 and random access memory (RAM) 1825. A basic input/output system 1826 (BIOS), containing the basic routines that help to transfer information between elements within the computer 1820, such as during start-up, is stored in ROM 1824.

The computer 1820 may further include a hard disk drive 1827 for reading from and writing to a hard disk (not shown), a magnetic disk drive 1828 for reading from or writing to a removable magnetic disk 1829, and an optical disk drive 1830 for reading from or writing to a removable optical disk 1831 such as a CD-ROM or other optical media. The hard disk drive 1827, magnetic disk drive 1828, and optical disk drive 1830 are connected to the system bus 1823 by a hard disk drive interface 1832, a magnetic disk drive interface 1833, and an optical drive interface 1834, respectively. The drives and their associated computer-readable media provide non-volatile storage of computer readable instructions, data structures, program modules and other data for the computer 1820. As described herein, computer-readable media is an article of manufacture and thus not a transient signal.

Although the exemplary environment described herein employs a hard disk, a removable magnetic disk 1829, and a removable optical disk 1831, it should be appreciated that other types of computer readable media which can store data that is accessible by a computer may also be used in the exemplary operating environment. Such other types of media include, but are not limited to, a magnetic cassette, a flash memory card, a digital video or versatile disk, a Bernoulli cartridge, a random access memory (RAM), a read-only memory (ROM), and the like.

A number of program modules may be stored on the hard disk, magnetic disk 1829, optical disk 1831, ROM 1824 or RAM 1825, including an operating system 1835, one or more application programs 1836, other program modules 1837 and program data 1838. A user may enter commands and information into the computer 1820 through input devices such as a keyboard 1840 and pointing device 1842. Other input devices (not shown) may include a microphone, joystick, game pad, satellite disk, scanner, or the like. These and other input devices are often connected to the processing unit 1821 through a serial port interface 1846 that is coupled to the system bus, but may be connected by other interfaces, such as a parallel port, game port, or universal serial bus (USB). A monitor 1847 or other type of display device is also connected to the system bus 1823 via an interface, such as a video adapter 1848. In addition to the monitor 1847, a computer may include other peripheral output devices (not shown), such as speakers and printers. The exemplary system of FIG. 18 also includes a host adapter 1855, a Small Computer System Interface (SCSI) bus 1856, and an external storage device 1862 connected to the SCSI bus 1856.

The computer 1820 may operate in a networked environment using logical connections to one or more remote computers, such as a remote computer 1849 (i.e., the monitoring device 230). The remote computer 1849 may be a personal computer, a server, a router, a network PC, a peer device or other common network node, and may include many or all of the elements described above relative to the computer 1820, although only a memory storage device 1850 has been illustrated in FIG. 18. The logical connections depicted in FIG. 18 include a local area network (LAN) 1851 and a wide area network (WAN) 1852. Such networking environments are commonplace in offices, enterprise-wide computer networks, intranets, and the Internet.

When used in a LAN networking environment, the computer 1820 is connected to the LAN 1851 through a network interface or adapter 1853. When used in a WAN networking environment, the computer 1820 may include a modem 1854 or other means for establishing communications over the wide area network 1852, such as the Internet. The modem 1854, which may be internal or external, is connected to the system bus 1823 via the serial port interface 1846. In a networked environment, program modules depicted relative to the computer 1820, or portions thereof, may be stored in the remote memory storage device. It will be appreciated that the network connections shown are exemplary and other means of establishing a communications link between the computers may be used.

Computer 1820 may include a variety of computer readable storage media. Computer readable storage media can be any available media that can be accessed by computer 1820 and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1820. Combinations of any of the above should also be included within the scope of computer readable media that may be used to store source code for implementing the methods and systems described herein. Any combination of the features or elements disclosed herein may be used in one or more embodiments.

In describing preferred embodiments of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A first sporting apparatus, the first sporting apparatus comprising:
   a first monitoring device near an area of impact of the first sporting apparatus, the first monitoring device comprising:
      a processor; and
      a memory coupled with the processor, the memory comprising executable instructions that when executed by the processor cause the processor to effectuate operations comprising:
         capturing data of a pre-impact path of a swing of the first sporting apparatus;
         capturing data of a post-impact path of the swing of the first sporting apparatus;
         trimming the data of the post-impact path; and
         determining a hypothetical swing path of the swing of the first sporting apparatus based on the data of the pre-impact path, the trimmed data of the post-impact path, and further based on at least data of a second swing of the first sporting apparatus.

2. The first sporting apparatus of claim 1, wherein the determining of the hypothetical swing path of the swing of the first sporting apparatus is additionally based on at least data of an impact of the swing of the first sporting apparatus with a sporting object.

3. The first sporting apparatus of claim 1, wherein trimming the data of the post-impact path comprises removing data captured during post-impact vibrations of the first sporting apparatus.

4. The first sporting apparatus of claim 1, wherein the hypothetical swing path is a hypothetical post-impact swing path.

5. A system comprising:
   a first sporting apparatus, the first sporting apparatus comprising:
      a first monitoring device, the first monitoring device comprising:
         a first processor; and
         a first memory coupled with the first processor, the first memory comprising executable instructions that when executed by the first processor cause the first processor to effectuate operations comprising:
            capturing data of a first pre-impact path of a first swing portion of a first swing of the first sporting apparatus; and
            capturing data of a first post-impact path of a second swing portion of the first swing of the first sporting apparatus; and
   a remote apparatus, the remote apparatus comprising:
      a remote processor; and
      a remote memory coupled with the remote processor, the remote memory comprising executable instructions that when executed by the remote processor cause the remote processor to effectuate operations comprising:
         receiving the data of the first pre-impact path and the data of the first post-impact path;
         trimming the data of the first post-impact path; and
         determining a hypothetical post-impact swing path of the first swing of the first sporting apparatus based on the data of the first pre-impact path, and the trimmed data of the first post-impact path, wherein the remote processor further effectuates operations comprising determining the hypothetical post-impact swing path of the first swing of the first sporting apparatus additionally based at least on data of a second swing of the first sporting apparatus.

6. The system of claim 5, wherein the first sporting apparatus comprises a golf club, a tennis racket, or a hockey stick.

7. The system of claim 5, wherein the first monitoring device is located at an area of impact for the first sporting apparatus.

8. The system of claim 5, wherein the remote processor further effectuates operations comprising determining the hypothetical post-impact swing path of the first swing of the first sporting apparatus additionally based on at least data of a portion of the first post-impact swing path, the at least data of the portion of the first post-impact swing path comprises data of when vibrations of the first sporting apparatus have ceased.

9. The system of claim 5, wherein the remote processor further effectuates operations comprising determining the hypothetical post-impact swing path of the first swing of the first sporting apparatus additionally based on data of a second monitoring device at a non-impact area of the first sporting apparatus.

10. The system of claim 5, wherein the remote processor further effectuates operations comprising providing instructions to display the hypothetical post-impact swing path.

11. A method comprising:
   a. capturing data of a first pre-impact path of a first swing of a sporting apparatus comprising a monitoring device, the monitoring device being sized, shaped, and positioned relative to the sporting apparatus such that the sporting apparatus comprising the monitoring device exhibits swing characteristics similar to a comparable sporting apparatus without the monitoring device;
   b. capturing data of a first post-impact path of the first swing of the sporting apparatus;
   c. trimming the data of the first post-impact path;
   d. determining, based at least in part on the data of the first pre-impact path and trimming the data of the first post-impact path, a first hypothetical swing path of the sporting apparatus;
   e. capturing data of a second pre-impact path based on a second swing of the sporting apparatus;
   f. capturing data of a second post-impact path based on the second swing of the sporting apparatus;
   g. trimming the data of the second post-impact path; and
   h. determining, based at least in part on the first hypothetical swing path, the data of the second pre-impact path and trimming the data of the second post-impact path, a second hypothetical swing path of the sporting apparatus.

12. The method of claim 11 further comprising displaying the first hypothetical swing path on a display.

13. The method of claim 11 wherein trimming the data of the first post-impact path comprises removing data captured during substantial post-impact vibrations of the sporting apparatus.

14. The method of claim 11, wherein the sporting apparatus comprises a baseball bat or a shoe.

15. The method of claim 11 wherein the sporting apparatus comprises a golf club.

16. A system comprising:
   a first sporting apparatus, the first sporting apparatus comprising:
      a first monitoring device, the first monitoring device comprising:
         a first processor; and
         a first memory coupled with the first processor, the first memory comprising executable instructions that when executed by the first processor cause the first processor to effectuate operations comprising:
            capturing data of a first pre-impact path of a first swing portion of a first swing of the first sporting apparatus; and
            capturing data of a first post-impact path of a second swing portion of the first swing of the first sporting apparatus; and
   a remote apparatus, the remote apparatus comprising:
      a remote processor; and
      a remote memory coupled with the remote processor, the remote memory comprising executable instructions that when executed by the remote processor cause the remote processor to effectuate operations comprising:
         receiving the data of the first pre-impact path and the data of the first post-impact path;
         trimming the data of the first post-impact path; and
         determining a hypothetical post-impact swing path of the first swing of the first sporting apparatus based on the data of the first pre-impact path, and the trimmed data of the first post-impact path, wherein the remote processor further effectuates operations comprising determining the hypothetical post-impact swing path of the first swing of the first sporting apparatus additionally based on at least data of a second swing of the first sporting apparatus.

17. The system of claim 16, wherein the remote processor further effectuates operations comprising determining the hypothetical post-impact swing path of the first swing of the first sporting apparatus additionally based at least on data of a portion of the first post-impact swing path, wherein the data of the portion of the first post-impact swing path comprising data of when vibrations of the first sporting apparatus have ceased.

18. The system of claim 16, wherein the first monitoring device is located at an area of impact for the first sporting apparatus.

19. The system of claim 16, wherein the first sporting apparatus comprises a golf club, a tennis racket, a squash racket, or a racquet ball racket.

20. The system of claim 16, wherein the remote processor further effectuates operations comprising determining the hypothetical post-impact swing path of the first swing of the first sporting apparatus additionally based on data of a second monitoring device at a non-impact area of the first sporting apparatus.

* * * * *